United States Patent
McNair et al.

(10) Patent No.: US 11,398,310 B1
(45) Date of Patent: Jul. 26, 2022

(54) CLINICAL DECISION SUPPORT FOR SEPSIS

(71) Applicant: CERNER INNOVATION, INC., Kansas City, KS (US)

(72) Inventors: Douglas S. McNair, Seattle, WA (US); John Christopher Murrish, Overland Park, KS (US); Kanakasabha Kailasam, Olathe, KS (US); Mark A. Hoffman, Lee's Summit, MO (US); Hugh Ryan, Lee's Summit, MO (US); Bharat Sutariya, Parkville, MO (US); Leo V. Perez, Platte City, MO (US); John Kuckelman, Shawnee, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 16/868,642

(22) Filed: May 7, 2020

Related U.S. Application Data

(63) Continuation of application No. 13/963,732, filed on Aug. 9, 2013, now Pat. No. 10,734,115, which is a
(Continued)

(51) Int. Cl.
  *G16H 50/30* (2018.01)
(52) U.S. Cl.
  CPC .................. *G16H 50/30* (2018.01)
(58) Field of Classification Search
  USPC ........................................................ 705/2, 3
  See application file for complete search history.

(56) References Cited

U.S. PATENT DOCUMENTS

| 4,839,853 A | 6/1989 | Deerwester et al. |
| 5,243,565 A | 9/1993 | Yamamoto |

(Continued)

FOREIGN PATENT DOCUMENTS

| EP | 1043666 A2 | 10/2000 |
| EP | 2365456 A2 | 9/2011 |

(Continued)

OTHER PUBLICATIONS

Zulaiha Ali Othman, Azuraliza Abu Bakar, Abdul Razak Hamdan, Khairuddin Omar, Nor Liyana Mohd Shuib, "Agent Based Preprocessing," International Conference on Intelligent and Advanced Systems 2007 (Year: 2007).*

(Continued)

*Primary Examiner* — Joshua B Blanchette
(74) *Attorney, Agent, or Firm* — Shook, Hardy & Bacon L.L.P.

(57) ABSTRACT

Methods are provided for validating theoretical improvements in the decision-support processes facilitating surveillance and monitoring of a patient's risk for developing a particular disease or condition and detecting the disease or condition. Patient information is received from a source and populated into an active risk assessment that monitors the patient's risk for developing Sepsis. At least a first and second set of actionable criteria for determining a patient's risk for developing sepsis are received. For each set of actionable criteria, it is determined that actionable criteria have been met. In some embodiments, software agents, operating in a multi-agent computing platform, perform each determination of whether actionable criteria are met. In some embodiments, in response to actionable criteria being met, a notification or alert is provided, and in some embodiments the results of the determinations of each set of
(Continued)

actionable criteria are provided to facilitate validation of theoretical improvements.

20 Claims, 19 Drawing Sheets

Related U.S. Application Data continuation-in-part of application No. 13/269,262, filed on Oct. 7, 2011, now abandoned, and a continuation-in-part of application No. 13/250,072, filed on Sep. 30, 2011, now Pat. No. 10,431,336.

(60) Provisional application No. 61/681,446, filed on Aug. 9, 2012, provisional application No. 61/391,392, filed on Oct. 8, 2010, provisional application No. 61/389,053, filed on Oct. 1, 2010.

(56) References Cited

U.S. PATENT DOCUMENTS

| | | |
|---|---|---|
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg, III et al. |
| 6,039,688 A | 3/2000 | Douglas et al. |
| 6,122,628 A | 9/2000 | Castelli et al. |
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,915,254 B1 | 7/2005 | Heinze et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,386,522 B1 * | 6/2008 | Bigus .............. G06N 5/043 706/15 |
| 7,440,947 B2 | 10/2008 | Adcock et al. |
| 7,447,643 B1 | 11/2008 | Olson et al. |
| 7,496,561 B2 | 2/2009 | Caudill et al. |
| 7,529,765 B2 | 5/2009 | Brants et al. |
| 7,555,425 B2 | 6/2009 | Oon |
| 7,558,778 B2 | 7/2009 | Carus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,015,136 B1 | 9/2011 | Baker et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | McNair et al. |
| 9,375,142 B2 | 6/2016 | Schultz et al. |
| 9,542,647 B1 | 1/2017 | Mirhaji |
| 9,734,146 B1 | 8/2017 | McNair et al. |
| 10,249,385 B1 | 4/2019 | McNair et al. |
| 10,268,687 B1 | 4/2019 | McNair et al. |
| 10,431,336 B1 | 10/2019 | Murrish et al. |
| 10,446,273 B1 | 10/2019 | McNair et al. |
| 10,628,553 B1 | 4/2020 | Murrish et al. |
| 10,734,115 B1 | 8/2020 | McNair et al. |
| 10,769,241 B1 | 9/2020 | McNair |
| 10,854,334 B1 | 12/2020 | McNair et al. |
| 10,946,311 B1 | 3/2021 | McNair |
| 10,957,449 B1 | 3/2021 | McNair et al. |
| 2002/0007284 A1 | 1/2002 | Schurenberg et al. |
| 2002/0023067 A1 | 2/2002 | Garland et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 | 9/2002 | Leveque et al. |
| 2003/0023571 A1 | 1/2003 | Barnhill |
| 2003/0038308 A1 | 2/2003 | Kim |
| 2003/0055679 A1 | 3/2003 | Soll et al. |
| 2003/0163057 A1 | 8/2003 | Flick et al. |
| 2003/0212580 A1 | 11/2003 | Shen |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0055246 A1 | 3/2005 | Simon |
| 2005/0119534 A1 | 6/2005 | Trost et al. |
| 2005/0144042 A1 | 6/2005 | Joffe et al. |
| 2005/0256740 A1 | 11/2005 | Kohan et al. |
| 2005/0272984 A1 | 12/2005 | Huiku |
| 2005/0288910 A1 | 12/2005 | Schlessinger et al. |
| 2006/0020465 A1 | 1/2006 | Cousineau et al. |
| 2006/0036619 A1 | 2/2006 | Fuerst et al. |
| 2006/0064447 A1 | 3/2006 | Malkov |
| 2006/0074824 A1 | 4/2006 | Li |
| 2006/0129427 A1 | 6/2006 | Wennberg |
| 2006/0161457 A1 | 7/2006 | Rapaport et al. |
| 2006/0173663 A1 | 8/2006 | Langheier et al. |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 | 10/2007 | Pendergast et al. |
| 2008/0021288 A1 | 1/2008 | Bowman et al. |
| 2008/0046292 A1 * | 2/2008 | Myers .............. G06F 16/283 705/3 |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147441 A1 | 6/2008 | Kil |
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cater |
| 2008/0249376 A1 | 10/2008 | Zaleski |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |

(56) References Cited

U.S. PATENT DOCUMENTS

| | | |
|---|---|---|
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |
| 2009/0112892 A1 | 4/2009 | Cardie et al. |
| 2009/0125333 A1 | 5/2009 | Heywood et al. |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299767 A1* | 12/2009 | Michon .................. G16H 50/80 705/3 |
| 2009/0299977 A1 | 12/2009 | Rosales |
| 2009/0304246 A1 | 12/2009 | Walker et al. |
| 2009/0313041 A1 | 12/2009 | Eder |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0121883 A1 | 5/2010 | Cutting et al. |
| 2010/0131434 A1 | 5/2010 | Magent et al. |
| 2010/0131438 A1 | 5/2010 | Pandya et al. |
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0153133 A1 | 6/2010 | Angell et al. |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0274576 A1 | 10/2010 | Young |
| 2010/0293003 A1 | 11/2010 | Abbo |
| 2010/0299155 A1 | 11/2010 | Findlay et al. |
| 2010/0324938 A1 | 12/2010 | Ennett et al. |
| 2011/0010401 A1 | 1/2011 | Adams et al. |
| 2011/0015937 A1 | 1/2011 | Janas, III et al. |
| 2011/0046979 A1 | 2/2011 | Tulipano et al. |
| 2011/0067108 A1 | 3/2011 | Hoglund |
| 2011/0077973 A1 | 3/2011 | Breitenstein et al. |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1 | 1/2012 | Ryan et al. |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | McDonald et al. |
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2013/0006911 A1 | 1/2013 | Christie, IV et al. |
| 2013/0023434 A1 | 1/2013 | Van Laar |
| 2013/0031613 A1 | 1/2013 | Shanabrook et al. |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132312 A1 | 5/2013 | Lee et al. |
| 2013/0132323 A1 | 5/2013 | Soto et al. |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0124269 A1 | 5/2017 | McNair et al. |
| 2019/0336085 A1 | 11/2019 | Kayser et al. |
| 2020/0335179 A1* | 10/2020 | Stojadinovic .......... G16B 40/00 |
| 2021/0177338 A1 | 6/2021 | Pagi et al. |

FOREIGN PATENT DOCUMENTS

| | | | |
|---|---|---|---|
| WO | 2006/002465 A1 | 1/2006 | |
| WO | 2009/112977 A1 | 9/2009 | |
| WO | WO-2010045463 A2 * | 4/2010 | ............ G16B 40/00 |
| WO | 2012/122122 A1 | 9/2012 | |
| WO | 2012/122195 A1 | 9/2012 | |
| WO | 2012/122196 A2 | 9/2012 | |

OTHER PUBLICATIONS

Uhrmacher et al., "Distributed, Parallel Simulation of Multiple, Deliberative Agents", Proceedings of the fourteenth workshop on Parallel and distributed simulationMay 2000 pp. 101-108 (Year: 2000).*

Non-Final Office Action received for U.S. Appl. No. 16/819,890, dated Sep. 29, 2020, 12 pages.

Non-Final Office Action received for U.S. Appl. No. 15/386,876, dated Sep. 14, 2020, 15 pages.

Notice of Allowance received for U.S. Appl. No. 14/148,046, dated Oct. 7, 2020, 11 pages.

The Comprehensive R Archive Network, R, Available online at: <http://cran.r-project.org>. Retrieved on Feb. 27, 2020, 1 page.

Cook et al., "Making Prophecies with Decision Predicates", ACM 978-1-4503-0490-0/11/01, Jan. 2011, 14 pages.

Prados-Suarez et al., "Contextualized Access to Electronical Health Records in Cardiology", IEEE Transactions on Information Technology in Biomedicine, vol. 16, No. 3, doi: 10.1109/TITB.2011.2178033., May 2012, pp. 401-412.

Final Office Action received for U.S. Appl. No. 15/855,720, dated Jul. 2, 2020, 15 pages.

Appavoo et al., "Enabling Autonomic Behavior in Systems Software With Hot Swapping", IBM Systems Journal, vol. 42, No. 1, 2003, pp. 60-76.

Final Office Action received for U.S. Appl. No. 13/269,244, dated Aug. 12, 2020, 18 pages.

Final Office Action received for U.S. Appl. No. 14/148,059, dated Jul. 16, 2020, 16 pages.

Notice of Allowance received for U.S. Appl. No. 14/148,020, dated Jul. 22, 2020, 10 pages.

Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#X0SgnSgzY2x>, Mar. 2013, 3 pages.

Final Office Action received for U.S. Appl. No. 14/148,039, dated Feb. 1, 2021, 17 pages.

Final Office Action received for U.S. Appl. No. 15/386,876, dated Jan. 11, 2021, 16 pages.

(56) References Cited

OTHER PUBLICATIONS

Summons to Attend Oral Proceedings received for European Patent Application No. 14835964.9, dated Jan. 13, 2021, 12 pages.
Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.
Ta et al., "Data Descriptor: Columbia Open Health Data, Clinical Concept Prevalence and Co-occurrence from Electronic Health Records", Scientific data, vol. 5, 180273, doi: 10.1038/sdata.2018.273, Nov. 27, 2018, pp. 1-17.
Final Office Action received for U.S. Appl. No. 14/209,568, dated Jul. 12, 2021, 9 pages.
Final Office action received for U.S. Appl. No. 14/555,058, dated Jun. 22, 2021, 12 pages.
Non-Final Office action received for U.S. Appl. No. 16/237,304, dated Jul. 7, 2021, 13 pages.
Non-Final Office Action received for U.S. Appl. No. 16/819,890, dated Jun. 24, 2021, 14 pages.
Notice of Allowance received for U.S. Appl. No. 15/855,720, dated Jun. 1, 2021, 15 pages.
Preinterview First Office Action received for U.S. Appl. No. 16/601,311, dated Jun. 15, 2021, 4 pages.
Duff, SI., "Development and history of sparse direct methods", SIAM Conference on Applied Linear Algebra, Available online at: <http://www,numerical.rl.ac.uk/people/isd/isd,html>, Oct. 26-29, 2009, 44 pages.
Shirabad et al., "Implementing an Integrative Multi-agent Clinical Decision Support System with Open Source Software", Journal of Medical Systems 36, Available online at: <https://doi.org/10.1007/s10916-010-9452-9>, 2012, pp. 123-137.
Xue et al., "Fast Query by Example of Environmental Sounds via Robust and Efficient Cluster-based Indexing", 2008 IEEE, International Conference on Acoustics, Speech and Signal Processing, Available online at: <doi: 10.1109/ICASSP.2008.4517532>, 2008, pp. 5-8.
Notice of Allowance received for U.S. Appl. No. 16/588,647, dated Apr. 1, 2021, 21 pages.
Notice of Allowance received for U.S. Appl. No. 14/982,982, dated Sep. 13, 2021, 15 pages.
Pre-Interview First Office action received for U.S. Appl. No. 17/011,474, dated Sep. 28, 2021, 4 pages.
John et al., "Neuro-Fuzzy Clustering of Radiographic Tibia Image Data Using Type 2 Fuzzy Sets", Information Sciences, vol. 125, Issues 1-4, 2000, ISSN 0020-0255, Available on Internet at: <https://www.sciencedirect.com/science/article/pii/S002002550000009>, 2000, pp. 65-82.
Abbott et al., "Sequence Analysis and Optimal Matching Methods in Sociology, Review and Prospect", Sociological Methods & Research, vol. 29, Issue 1, Aug. 1, 2000, pp. 3-33.
Agrawal et al., "Fast Discovery of Association Rules", Advances in Knowledge Discovery and Data Mining, Feb. 1996, pp. 307-328.
Aronson, Alan R., "MetaMap: Mapping Text to the UMLS Metathesaurus", Jul. 14, 2006, pp. 1-26.
Arpaia et al. "Multi-Agent Remote Predictive Diagnosis of Dangerous Good Transports", Instrumentation and Measurement Technology Conference Proceedings, vol. 3, May 17-19, 2005, pp. 1685-1690.
Berchtold et al., "The Mixture Transition Distribution Model for High-Order Markov Chains and Non-Gaussian Time Series", Statistical Science, vol. 17, No. 3, 2002, pp. 328-356.
Berry et al., "Care Coordination for Patients With Complex Health Profiles in Inpatients and Outpatient Settings", Mayo Clinic Proceedings, vol. 88, No. 2, Feb. 2013, pp. 1-11.
Billari et al., "Timing, Sequencing, and Quantum of Life Course Events: A Machine-Learning Approach", European Journal of Population, vol. 22, Mar. 2006, pp. 37-65.
Cohen et al., "Integrated Complex Care Coordination For Children With Medical Complexity: A Mixed-Methods Evaluation of Tertiary Care-Community Collaboration", BMC Health Services Research, vol. 12, Article No. 366, Oct. 23, 2012, 23 pages.
Deville et al., "Correspondence Analysis with an Extension Towards Nominal Time Series", Journal of Econometrics, vol. 22, 1983, pp. 169-189.
Dijkstra et al., "Measuring the Agreement Between Sequences", Sociological Methods & Research, vol. 24, No. 2, Nov. 1995, pp. 214-231.
Dvorak et al., "Football Injuries and Physical Symptoms: A Review of the Literature", The American Journal of Sports Medicine, vol. 28, No. 5, 2000, pp. S3-S9.
Dvorak et al., "Risk Factor Analysis for Injuries in Football Players:Possibilities for a Prevention Program", The American Journal of Sports Medicine, vol. 28, No. 5, 2000, pp. S69-S74.
Han et al., "Frequent Pattern Mining: Current Status and Future Directions", Data Mining and Knowledge Discovery, vol. 15, Jan. 27, 2007, pp. 55-86.
Hawkins et al., "A Prospective Epidemiological Study of Injuries in Four English Professional Football Clubs", British Journal of Sports Medicine, vol. 33, 1999, pp. 196-203.
Huyse et al., "COMPRI—An Instrument to Detect Patients With Complex Care Needs: Results from a European Study", Psychosomatics, vol. 42, No. 3, May-Jun. 2001, pp. 222-228.
Junge et al., "Soccer Injuries: A Review on Incidence and Prevention", Sports Medicine, vol. 34, No. 13, 2004, pp. 929-938.
Kang et al., "Mining Based Decision Support Multi-agent System for Personalized e-Healthcare Service", Proceedings of the 2nd KES International conference on Agent and Multi-Agent Systems: Technologies and Applications, 2008, pp. 733-742.
Kiran et al., "An Improved Multiple Minimum Support Based Approach to Mine Rare Association Rules", IEEE Symposium on Computational Intelligence and Data Mining, 2009, 8 pages.
Mabry et al., "Clinical Decision Support with IM-Agents and ERMA Multi-agents", Proceedings of the 17th IEEE Symposium on Computer-Based Medical Systems, 2004, 6 pages.
Nealon et al., "Agent-Based Applications in Health Care", Applications of Software Agent Technology in the Health Dare Domain, 2003, pp. 1-17.
Nielsen et al., "Epidemiology and Traumatology of Injuries in Soccer", The American Journal of Sports Medicine, vol. 17, No. 6, 1989, pp. 803-807.
Notice of Allowance received for U.S. Appl. No. 13/269,244, dated Dec. 14, 2021, 9 pages.
Ohno-Machado, Lucila, "Realizing the Full Potential of Electronic Health Records: The Role of Natural Language Processing", Journal of American Medical Information Association, vol. 18, No. 5, Sep. 2011, p. 539.
Roever, Christian, "Package 'Bayesian Spectral Inference'", CRAN, Available online at: <r-project.org>, Feb. 21, 2013, pp. 1-27.
Sariyar et al., "The RecordLinkage Package: Detecting Errors in Data", The R Journal, vol. 2, No. 2, Dec. 2010, pp. 61-67.
Seibig et al., "Collection of Annotated Data in a Clinical Validation Study for Alarm Algorithms in Intensive Care—a Methodologic Framework", Journal of Critical Care, vol. 25, Issue 1, 2010, pp. 128-135.
Zaki, Mohammed J., "Spade: An Efficient Algorithm for Mining Frequent Sequences", Machine Learning, vol. 42, 2001, pp. 31-60.
Notice of Allowance received for U.S. Appl. No. 16/793,870, dated Feb. 8, 2022, 18 pages.
Pre-Interview First Office action received for U.S. Appl. No. 16/714,221, dated Jan. 27, 2022, 5 pages.
First Action Interview Office Action received for U.S. Appl. No. 16/714,221, dated Apr. 4, 2022, 19 pages.
Non-Final Office Action received for U.S. Appl. No. 16/717,299, dated Apr. 27, 2022, 10 pages.
Non-Final Office Action received for U.S. Appl. No. 16/819,890, dated Apr. 28, 2022, 17 pages.

\* cited by examiner

2/5 SIRS CRITERIA PRESENT – NO ORGAN DYSFUNCTION — 1010

SIRS — 1012
- HR-100BMP
- TEMPERATURE-38.9 C
- RESPIRATIONS-WNL
- GLUCOSE-WNL
- WBC-WNL

ORGAN DYSFUNCTION — 1014
- LACTATE-WNL
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT — 1016

"THIS PATIENT HAS MET THE FOLLOWING SIRS CRITERIA (DISPLAY CRITERIA MET). CONTACT THE PHYSICIAN AND CONSIDER ORDERING THE FOLLOWING LABORATORY TESTS".

- LACTATE
- CREATININE
- BILIRUBIN
- PLATELET COUNT
- PTT
- BLOOD CULTURES
- UA

*FIG. 10.*

3/5 SIRS CRITERIA PRESENT – NO ORGAN DYSFUNCTION ⟵ 1110

SIRS ⟵ 1112
- HR-100BMP
- TEMPERATURE-38.9 C
- RESPIRATIONS-26BPM
- GLUCOSE-WNL
- WBC-WNL

ORGAN DYSFUNCTION ⟵ 1114
- LACTATE-WNL
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT ⟵ 1116

"THIS PATIENT HAS MET THE FOLLOWING SIRS CRITERIA (DISPLAY CRITERIA MET). CONTACT THE PHYSICIAN AND CONSIDER ORDERING THE FOLLOWING LABORATORY TESTS".

- LACTATE
- CREATININE
- BILIRUBIN
- PLATELET COUNT
- PTT
- BLOOD CULTURES
- UA

2/5 SIRS CRITERIA PRESENT – 1 ORGAN DYSFUNCTION

SIRS
- HR-100BMP
- TEMPERATURE-38.9 C
- RESPIRATIONS-WNL
- GLUCOSE-WNL
- WBC-WNL

ORGAN DYSFUNCTION
- LACTATE-3.1MMOL/L
- CREATININE-WNL
- PLATELET COUNT-WNL
- BILIRUBIN-WNL
- PTT-WNL
- SYSTOLIC BLOOD PRESSURE-WNL
- MEAN ARTERIAL PRESSURE-WNL
- MENTAL STATUS CHANGE-WNL
- FIO2 RATIO-WNL

ALERT

"THIS PATIENT HAS MET THE CRITERIA FOR SEPSIS (DISPLAY SIRS AND ORGAN DYSFUNCTION CRITERIA MET). PLEASE EVALUATE THE PATIENT AND NOTIFY THE PHYSICIAN IMMEDIATELY.

EARLY GOAL DIRECTED THERAPY IS ESSENTIAL FOR THE TREATMENT OF SEPSIS. TIME DEPENDANT INTERVENTION MAY IMPACT PATIENT OUTCOME".

*FIG. 12.*

NOTIFICATION MESSAGE

SUBJECT: SEPSIS SCREENING ACUTE CARE
PRIORITY STATUS: HIGH   PRIORITY VALUE: 80
EVENT DATE/TIME: 11/19/2010 1:35:38 PM
MESSAGE CLASS/SUBCLASS: APPLICATION

ALERT

1310 —
NAME: MCKENNA, STEVE
DATE: NOVEMBER 19, 2010 13:35:38 CST
MRN: 00001694
BIRTH DATE: JANUARY 04, 1973
AGE: 37
LOCATION: BASELINE WEST M; 4 NORTH – ICU; 404
THIS PATIENT HAS MET THE CRITERIA FOR SEPSIS. PLEASE EVALUATE PATIENT AND NOTIFY THE PHYSICIAN IMMEDIATELY TO REVIEW THE SEPSIS MANAGEMENT POWERPLAN THAT HAS BEEN SUGGESTED FOR THIS PATIENT.

1312 —
ALERT FOR 2/5 SIRS CRITERIA: "THIS PATIENT HAS MET 2/5 SIRS CRITERIA (DISPLAY CRITERIA MET). CONTACT THE PHYSICIAN AND CONSIDER ORDERING THE FOLLOWING LABORATORY TESTS".
- LACTATE
- CREATININE
- BILIRUBIN
- PLATELET COUNT
- PTT
- BLOOD CULTURES
- UA

EARLY GOAL DIRECTED THERAPY IS ESSENTIAL FOR THE TREATMENT OF SEPSIS. TIME DEPENDANT INTERVENTION MAY IMPACT PATIENT OUTCOME.

1314 —
SIRS CRITERIA
 11/19/10 1328 BLOOD GLUCOSE, CAPILLARY = 125 MG/DL (H) [GREATER THAN 120]
 11/19/10 1328 PERIPHERAL PULSE RATE = 130 BPM (H) [GREATER THAN 90]
 11/19/10 1321 TEMPERATURE ORAL = 39 C (H) [GREATER THAN 38.3]
 11/19/10 1328 RESPIRATORY RATE = 30 BPM (H) [GREATER THAN 20]
ORGAN DYSFUNCTION
 11/19/10 1328 SYSTOLIC BLOOD PRESSURE = 68 MMHG (L) [LESS THAN 90]
 11/19/10 1328 MEAN ARTERIAL PRESSURE, CUFF = 43 MMHG (L) [LESS THAN 65]

*FIG. 13.*

CLINICAL DECISION SUPPORT FOR SEPSIS

CROSS-REFERENCE TO RELATED APPLICATIONS AND PRIORITY CLAIM

Cross-Reference to Related Applications

This application is a continuation of, and claims priority from, U.S. application Ser. No. 13/963,732, titled "CLINICAL DECISION SUPPORT FOR SEPSIS," filed Aug. 9, 2013; which is a continuation-in-part of, and claims priority from, U.S. application Ser. No. 13/269,262, titled "MULTI-SITE CLINICAL DECISION SUPPORT FOR SEPSIS," filed Oct. 7, 2011; which claims the benefit of U.S. Provisional Application No. 61/391,392, filed Oct. 8, 2010. Application Ser. No. 13/963,732 claims the benefit of U.S. Provisional Application No. 61/681,446, filed Aug. 9, 2012. Additionally, U.S. application Ser. No. 13/963,732 is a continuation-in-part of, and claims priority from, U.S. application Ser. No. 13/250,072 (now U.S. Pat. No. 10,431,336), titled "COMPUTERIZED SYSTEMS AND METHODS FOR FACILITATING CLINICAL DECISION MAKING," filed Sep. 30, 2011; which claims the benefit of U.S. Provisional Application No. 61/389,053, filed Oct. 1, 2010. Each of these references are hereby expressly incorporated by reference in their entirety. This application is related by subject matter to U.S. application Ser. No. 13/269,244, entitled "MULTI-SITE CLINICAL DECISION SUPPORT," filed Apr. 12, 2012, and is herein incorporated by reference in its entirety.

INTRODUCTION

The benefits of clinical decision support have been widely demonstrated. Current clinical decision support (CDS) systems operate within the parameters of the information system of a single medical organization. For instance, a patient may have an electronic medical record (EMR) with his or her primary care physician, but this EMR may not be shared with any other medical organizations that are involved with treating the patient, such as an emergency room, an urgent care clinic, a specialist, etc. As such, patient information is typically not shared between facilities, which may impair clinicians in their treatment of patients, as clinicians are unable to see the full scope of the patient's current medical conditions. For example, a patient may have a primary care physician, but may have an urgent medical situation and may go to an urgent care clinic one day and to an emergency room the next day for complications from a procedure performed by a specialist. This scenario is commonplace. Additionally, the case is rare when a patient is seen and treated by multiple clinicians who all use a common medical record system. Moreover, the monitoring for and detection of certain conditions, such as Sepsis, can involve inputting diverse reference ranges of monitored variables by different health care providers, which can result in different outcomes, i.e., this patient is or is not developing Sepsis, from using the different reference ranges.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In brief and at a high level, this disclosure describes, among other things, systems methods for validating theoretical improvements in the decision-support processes facilitating surveillance and monitoring of a patient's risk for developing a particular disease or condition and detecting the disease or condition. Often, patients are treated at multiple health care facilities, such as hospitals, doctors' offices, urgent care clinics, or the like. These facilities oftentimes are not interrelated and thus do not share medical record systems. Embodiments of the present invention allow for patient information to be received at a monitoring system that monitors, by way of arrays, a patient's risk of developing a particular disease or condition. One exemplary condition is sepsis, which occurs in the presence of an infection with a Systemic Inflammatory Response Syndrome (SIRS) response. This monitoring allows for earlier detection of diseases and conditions so that a patient can be treated earlier, before progression of the disease or condition. Additionally, methods provide clinicians with decision support, such as suggested laboratory tests and other treatment options, based on the patient information.

BRIEF DESCRIPTION OF THE DRAWINGS

The present invention is described in detail below with reference to the attached drawing figures, wherein:

FIGS. 10-12 illustrate exemplary actionable criteria and alerts for a patient being at risk for developing sepsis, in accordance with embodiments of the present invention;

FIG. 13 is an exemplary screen display of an alert after determination that a patient is at risk for developing sepsis, in accordance with an embodiment of the present invention;

DETAILED DESCRIPTION

Figure 1:
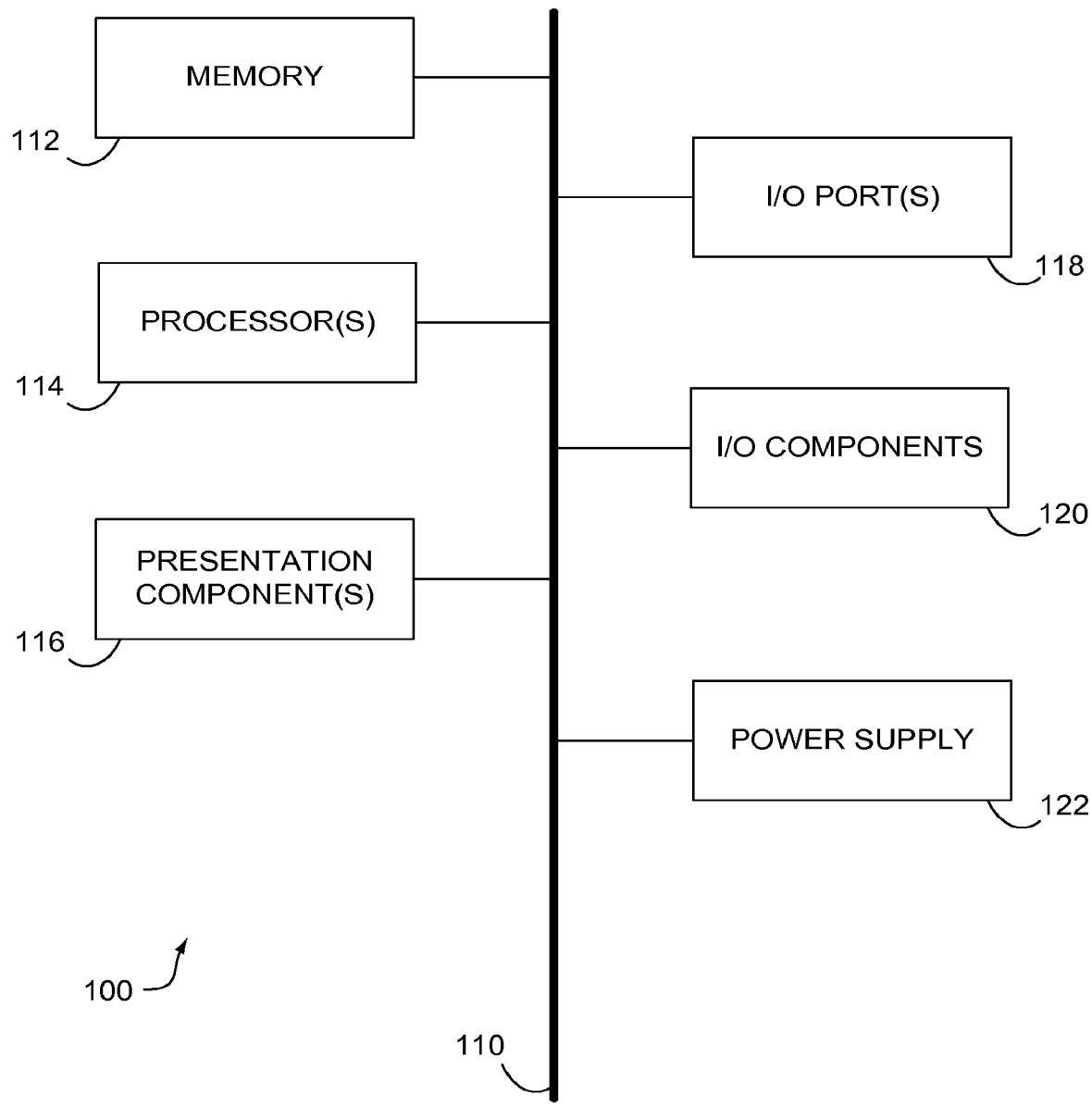
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide decision support capabilities that can benefit patient care across separate venues and organizations. For example, an algorithm in which risk is assessed by evaluating twenty clinical parameters and then escalating to the provider when any two of those parameters qualify for the triggering threshold can be implemented within an institution using a query of all information within that system available at the time that the triggering clinical action occurs. In the multi-site environment, in which each site may only evaluate a subset of the twenty parameters, it is very difficult to accomplish meaningful decision support using a query that is launched at the time of the triggering event.

As such, embodiments of the present invention allow for patient information from multiple, disparate medical organizations having different medical record systems to be used to determine when a patient is at risk for developing a particular disease or condition. When, based on the patient information, it is determined that the patient is at risk, an alert or notification is communicated to one or more of the medical organizations where the patient was treated, the primary care physician of the patient, or the patient. The patient, for instance, may take steps to return to a health care facility to be further evaluated. The clinicians, including physicians, nurses, physician assistants, etc., may receive individual alerts or notifications so that they can take action to further evaluate the patient. Similarly, the primary care physician may be alerted so that he or she can take steps to further evaluate the patient. The alerts are sent in near real-time so that time is not wasted, as many diseases or conditions have a higher success rate if the patient is treated in a timely and efficient manner.

In one embodiment of the present invention, a method is provided for enabling multi-site surveillance and decision support for a patient's medical care. The method includes receiving, from a first medical organization, a first set of patient information corresponding to a patient who has received medical treatment at the first medical organization, and determining that an active risk assessment array exists for the patient. The active risk assessment array represents the patient's risk of developing a particular disease or condition. Further, the method includes, for a first node of the active risk assessment array corresponding to the first set of patient information, populating a value of the first node with at least a portion of the first set of patient information. The method additionally includes receiving, from a second medical organization, a second set of patient information. The patient has received medical treatment at the second medical organization, and the first medical organization and the second medical organization maintain separate medical record systems. For a second node of the active risk assessment array corresponding to the second set of patient information, the method includes populating the value of the second node with at least a portion of the second set of patient information. The method also includes determining that actionable criteria for the particular disease or condition have been met based on at least the first and second nodes of the active risk assessment array and providing a notification that the actionable criteria have been met.

In another embodiment of the present invention, one or more computer storage media are provided having computer-executable instructions embodied thereon, that when executed by a computing system having a processor and memory, cause the computing system to perform a method for enabling multi-site surveillance and decision support for a patient's medical care. The method includes receiving a first set of patient information for a patient from a first medical organization, determining that an active risk assessment array does not exist for the patient, and creating the active risk assessment array for the patient for a particular condition or disease for which the patient is to be monitored. Further, the method includes populating values of a first set of nodes of the active risk assessment array with at least a portion of the first set of patient information. The method additionally includes receiving a second set of patient information for the patient from a second medical organization, determining that one or more nodes of the active risk assessment array correspond to at least a portion of the second set of patient information, and populating values of a second set of nodes of the active risk assessment array with the at least the portion of the second set of patient information. Even further, the method includes, based on the values of the first set of nodes and the second set of nodes, determining that the patient has met actionable criteria for being at risk for the particular disease or condition represented by the active risk assessment array. The method also includes notifying one or more of a primary care physician of the patient, the patient, the first medical organization, or the second medical organization that the actionable criteria have been met.

In yet another embodiment of the present invention, one or more computer storage media are provided having computer-executable instructions embodied thereon, that when executed by a computing system having a processor and memory, cause the computing system to perform a method for enabling multi-site surveillance and decision support for a patient's medical care. The method includes receiving a first set of patient information from a first medical organization for a patient and determining whether an active risk assessment array currently exists for the patient. If the active risk assessment array currently exists for the patient, the method includes accessing the active risk assessment array. If, however, the active risk assessment array currently does not exist for the patient, the method includes creating the active risk assessment array for a particular disease or condition for which the patient is to be monitored. Further, the method includes populating values of a first set of nodes of the active risk assessment array with the first set of patient information and receiving a second set of patient information from a second medical organization that maintains a distinct medical record system different from the first medical organization. Also, the method includes associating the first set of patient information with the second set of patient information based on knowledge that they correspond to a common patient and populating the values of a second set of nodes of the active risk assessment array with the second set of patient information. Based on the active risk assessment array, the method includes algorithmically determining that actionable criteria set by the first medical organization indicating that the patient is at risk for developing the particular disease or condition have been met. Additionally, the method includes notifying the first medical organization that the patient is at risk for the particular disease or condition.

Further, in another embodiment of the present invention, a method is provided for detecting sepsis in a patient based on multi-site surveillance. The method includes receiving, from a first medical organization, a first set of patient information corresponding to a patient who has received medical treatment at the first medical organization, and determining that an active risk assessment array exists for the patient, wherein the active risk assessment array represents the patient's risk of developing sepsis. The method also includes, for a first node of the active risk assessment array corresponding to the first set of patient information, populating a value of the first node with at least a portion of the first set of patient information and receiving, from a second medical organization, a second set of patient information. The patient has received medical treatment at the second medical organization, and the first medical organization and the second medical organization maintain separate medical record systems. Additionally, the method includes, for a second node of the active risk assessment array corresponding to at least a portion of the second set of patient information, populating the value of the second node with the at least the portion of the second set of patient information and determining that sepsis-specific actionable criteria have been met based on at least the values of the first node and the second node of the active risk assessment array. Also, the method includes providing a notification that the sepsis-specific actionable criteria have been met.

Additionally, in another embodiment of the present invention, one or more computer storage media are provided having computer-executable instructions embodied thereon, that when executed by a computing system having a processor and memory, cause the computing system to perform a method for detecting sepsis in a patient based on multi-site surveillance. The method includes receiving a first set of patient information for a patient from a first medical organization and based on the first set of patient information, determining that the patient is to be monitored for developing sepsis. The method further includes creating an active risk assessment array for the patient. The active risk assessment array comprises one or more nodes that allow for population of patient information that is specific to sepsis. Further, the method includes populating values of a first set of nodes of the active risk assessment array with at least a portion of the first set of patient information, receiving a second set of patient information for the patient from a second medical organization, and determining that the active risk assessment array that is specific to sepsis is currently active. Additionally, the method includes populating the values of a second set of nodes of the active risk assessment array with at least a portion of the second set of patient information and based on the values of the first set of nodes and the second set of nodes, determining that the patient has met actionable criteria for being at risk for developing sepsis. The method also includes notifying one or more of a primary care physician associated with the patient, the patient, the first medical organization, or the second medical organization that the patient has met the actionable criteria for developing sepsis. The notification is one or more of a flag in the patient's medical record, a message sent to a pager, an email, a text message, a message received at a message center, a telephone call, or a fax.

In yet another embodiment of the present invention, one or more computer storage media are provided having computer-executable instructions embodied thereon, that when executed by a computing system having a processor and memory, cause the computing system to perform a method for detecting sepsis in a patient based on multi-site surveillance. The method includes receiving a first set of patient information from a first medical organization for a patient, determining that, based on the first set of patient information, that the patient is to be monitored for developing sepsis, and determining whether an active risk assessment array corresponding to the patient's risk of developing sepsis currently exists for the patient. If the active risk assessment array currently exists for the patient, the method includes accessing the active risk assessment array, and if the active risk assessment array currently does not exist for the patient, the method includes creating the active risk assessment array corresponding to the patient's risk of developing sepsis. Further, the method includes populating values of a first set of nodes of the active risk assessment array with the first set of patient information and receiving a second set of patient information from a second medical organization that maintains a distinct medical record system different from the first medical organization. The method also includes associating the first set of patient information with the second set of patient information based on knowledge that they correspond to a common patient, populating the values of a second set of nodes of the active risk assessment array with the second set of patient information, and based on the active risk assessment array, algorithmically determining that actionable criteria set by the first medical organization for performing escalation actions has been met. The actionable criteria are met when the patient has a particular high risk for developing sepsis. Further, the method includes, in response to the actionable criteria being met, performing the escalation actions, wherein the escalation actions comprise notifying the first medical organization that the actionable criteria have been met for the patient.

Embodiments of the technology may take the form of, among other things: a method, system, or set of instructions embodied on one or more computer-readable media. Computer-readable media include both volatile and nonvolatile media, removable and nonremovable media, and contemplate media readable by a database, a switch, and various other network devices. By way of example, and not limitation, computer-readable media comprise media implemented in any method or technology for storing information, such as computer storage media. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

An exemplary operating environment suitable for implementing embodiments of the present invention is described below. Referring to the drawings in general, and initially to FIG. 1 in particular, an exemplary operating environment for implementing embodiments of the present invention is shown and designated generally as computing device 100.

Computing device 100 is but one example of a suitable computing environment and is not intended to suggest any limitation as to the scope of use or functionality of embodiments of the present invention. Neither should the computing environment 100 be interpreted as having any dependency or requirement relating to any one or combination of components illustrated.

Embodiments of the present invention may be described in the general context of computer code or machine-useable instructions, including computer-executable instructions such as program components, being executed by a computer or other machine, such as a personal data assistant or other handheld device. Generally, program components including routines, programs, objects, components, data structures, and the like refer to code that performs particular tasks, or implements particular abstract data types. Embodiments of the present invention may be practiced in a variety of system configurations, including handheld devices, consumer electronics, general-purpose computers, specialty computing devices, etc. Embodiments of the invention may also be practiced in distributed computing environments where tasks are performed by remote-processing devices that are linked through a communications network.

With continued reference to FIG. 1, computing device 100 includes a bus 110 that directly or indirectly couples the following devices: memory 112, one or more processors 114, one or more presentation components 116, input/output (I/O) ports 118, I/O components 120, and an illustrative power supply 122. Bus 110 represents what may be one or more buses (such as an address bus, data bus, or combination thereof). Although the various blocks of FIG. 1 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventors hereof recognize that such is the nature of the art and reiterate that the diagram of FIG. 1 is merely illustrative of an exemplary computing device that can be used in connection with one or more embodiments of the present invention. Distinction is not made between such categories as "workstation," "server," "laptop," "handheld device," etc., as all are contemplated within the scope of FIG. 1 and reference to "computer" or "computing device."

Memory 112 includes computer storage media in the form of volatile and/or nonvolatile memory. The memory may be removable, nonremovable, or a combination thereof. Exemplary hardware devices include solid-state memory, hard drives, optical-disc drives, etc. Computing device 100 includes one or more processors that read data from various entities such as memory 112 or I/O components 120. Presentation component(s) 116 present data indications to a user or other device. Exemplary presentation components include a display device, speaker, printing component, vibrating component, etc. I/O ports 118 allow computing device 100 to be logically coupled to other devices including I/O components 120, some of which may be built-in. Illustrative components include a microphone, joystick, game pad, satellite dish, scanner, printer, wireless device, etc.

Figure 2:
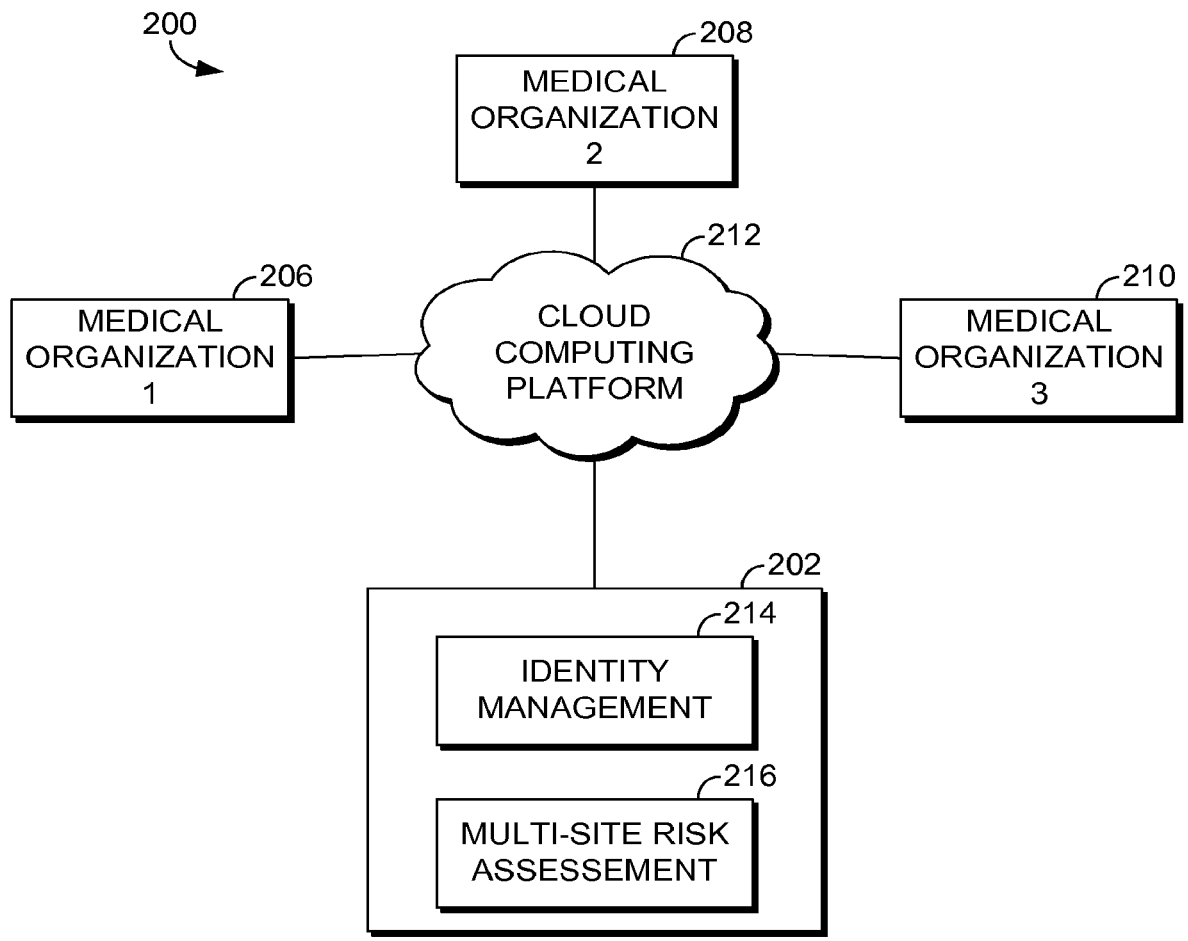
FIG. 2 is a block diagram showing an exemplary architecture for facilitating multi-site clinical decision support in accordance with an embodiment of the present invention.

Turning now to FIG. 2, a block diagram 200 is illustrated, in accordance with an embodiment of the present invention, showing an exemplary cloud-computing platform 212 for use by multi-site decision support manager 202. It will be understood and appreciated that the cloud-computing platform 212 shown in FIG. 2 is merely an example of one suitable computing system environment and is not intended to suggest any limitation as to the scope of use or functionality of embodiments of the present invention. For instance, the cloud-computing platform 212 may be a public cloud, a private cloud, or a dedicated cloud. Neither should the cloud-computing platform 212 be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, cloud-computing platform 212 comprises a cloud-computing network, which is known in the art as "the cloud."

The cloud-computing platform 212 includes a data center configured to host and support the operation of the manager 202. The manager 202 refers to any software, or portions of software, that run on top of, or access storage locations within, the platform 212. It will be appreciated that cloud-computing platform 212 may include multiple computing devices such as computing devices or portions of computing devices 100 shown in FIG. 1. Cloud-computing platform 212 may include virtual machines, such as software, application, operating system, or program that is executed by a processing unit to underlie the functionality of multi-site decision support manager 202. Further, the virtual machines may include processing capacity, storage locations, and other assets to support the multi-site decision support manager 202. In one instance, the computing devices of separate medical organizations, such as medical organizations 206, 208, and 210, host and support the operations of the multi-site data manager, while simultaneously hosting applications.

Figure 21A:
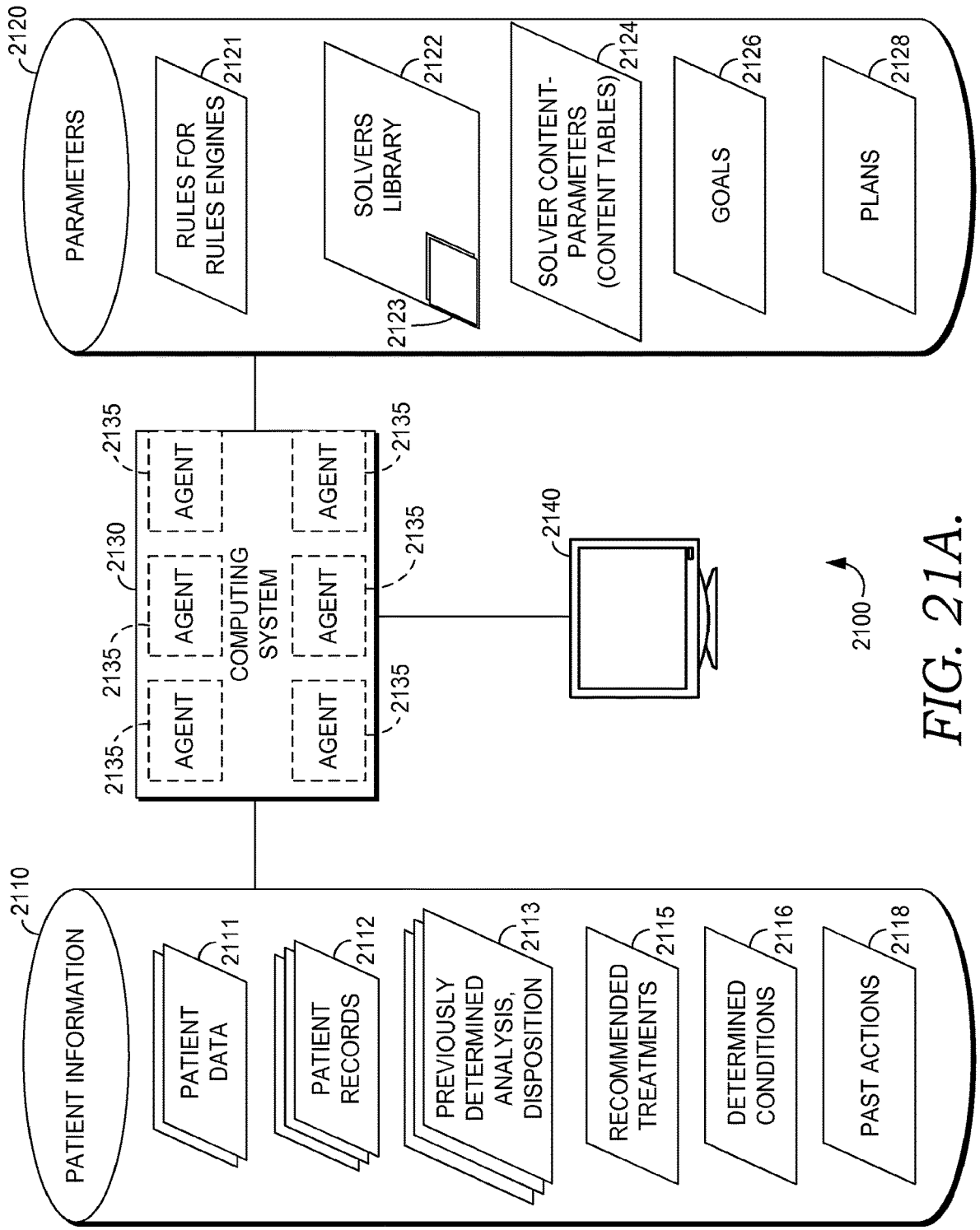
FIG. 21A depicts aspects of an illustrative operating environment suitable for practicing embodiments of the invention.

Turning briefly to FIG. 21A, in some embodiments, decision support manager 202 and computing platform 212 are implemented in operating environment 2100 using a multi-agent computer system such as exemplary computer system 2130 with one or more agents 2135, as shown in FIG. 21A and described in greater detail below. But it will be appreciated that computing system 2130 may also take the form of a single agent system or a non-agent system, as described in other embodiments herein. In some embodiments, computing platform 212 is embodied as computing system 2130, and in some embodiments, decision support manager 202 operates on an embodiment of computing system 2130, which runs on top of, or accesses storage locations within, the platform 212. Computing system 2130 may be embodied as a distributed computing system, a centralized computing system, a single computer such as a desktop or laptop computer or a networked computing system, described in other embodiments herein.

In some embodiments, computer system 2130 is a multi-agent computer system with agents 2135. Multi-agent computer system 2130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents 2135 based on beliefs, capabilities and choices that communicate via declarative messaging and use abstractions to allow for future adaptations and flexibility. An agent 2135 has its own thread of control which promotes the concept of autonomy.

Embodiments using multi-agent system 2130 provide capabilities to adapt the frequency and messages used for communication between the system 2130 and one or more users through user interface 2140, based on changes to the environment and provide capabilities to filter out noisy data, thereby providing more flexible and adaptable decision-making abilities. In some embodiments, this is accomplished by using leveraging preceptors and effectors. Preceptors or sensors, which in some embodiments may be agents, detect changes in an operating environment and pass this information to the agent system. Effectors, which in some embodiments may be agents 2135, respond directly to changes in an operating environment and consider goals and alternatives prior to implementing a change to the environment.

Embodiments using multi-agent system 2130 further have the capability of supporting intelligent information retrieval and filter out noisy data and utilize heuristics to narrow down a search space to assist in solving complex problems. The multi-agent system 2130 facilitates designing individual agent behaviors and their interactions with other agents 2135 and with users, through user interface 2140. In some embodiments, agents 2135 encoded with both declarative and procedural knowledge and can therefore learn by means of exploration of knowledge and imitation of other agents, for example, by leveraging aggregation of bottom-up and top-down modeling. In some embodiments, the agent system 2130 accepts an abstract workflow and converts it into an actual executable workflow, by for example, using contract and negotiation in multi-agent system 2130. The executable workflow may then leverage agents to run the actual workflow.

Furthermore, embodiments using multi-agent system 2130 coordinate the actions of the agents 2135 to cooperate to achieve common objectives, and negotiate to resolve conflicts, which allows for adaptability, flexibility, and organizational relationships. The transformation of heterogeneous knowledge and content into homogeneous knowledge and content is an important trait of the multi-agent system to provide interoperability. The multi-agent system 2130 operates to achieve its goals while still interacting with agents, including agents outside of the multi-agent system 2130 (not shown) and users at a higher degree of flexibility.

As a practical example, in some embodiments, a multi-agent system 2130 can be utilized to efficiently validate theoretical improvements to processes for detecting certain conditions, such as improvements to processes for determining likelihood of sepsis, described herein. In this example, input may be received, including patient information 2110 (described below) and one or more sets, thresholds, or ranges of variables, from parameters 2120 (described below), such as for example blood pressure, blood oxygen, temperature, or other variables used in the process for detecting sepsis described herein. Such variable sets, threshold(s), or range(s) may be received from one or more health care providers or from an agent, and, in some embodiments, may be specified in one or more content tables 2124 (described below). In some embodiments, the received variable set(s), threshold(s), or ranges may differ based on differing opinions, strategies, or condition-detection theories of the health care providers, or based on differences in the patient information 2110 available to each health care provider.

Continuing the example, in embodiments using multi-agent system 2130, for each of the variable set(s), range(s) or threshold(s), an agent 2135 may be invoked for determining likelihood of sepsis (or other condition) or for monitoring the patient for likelihood of sepsis (or other condition). In some embodiments the agents work in parallel, such that each agent operates with different set, range, or threshold values, thereby resulting in multiple evaluations for the likelihood of sepsis (or another condition) being carried out. In some embodiments, the results of the evaluations by the agents is compared to determine which set(s), range(s), or threshold(s) performs better for determining likelihood of sepsis (or another condition). Further, in some embodiments, multi-agent system 2130 learns the set(s), range(s), threshold(s) or other parameters 2120 and patient information 2110 that are more likely to result in an accurate diagnosis or detection of sepsis (or other condition). In some embodiments, the particular set(s), range(s), threshold(s), or other parameters 2120 which yield a more accurate determination of likelihood of sepsis (or another condition) are weighted, biased, or otherwise noted for future use in evaluating a patient for risk of sepsis (or other condition). Similarly, the particular process followed by the agent, for diagnosis or detection of sepsis (or other condition), which led to a more accurate result, is also noted. In this way, potential improvements in the sepsis detection processes (described herein, below) can be determined by experimentally modifying the input variable set(s), range(s), threshold(s), and other parameters 2120. In some embodiments, the agent responsible for implementing an improved detection process can be simply swapped with the agent handing the existing detection process.

In some embodiments, agents 2135 continually monitor events to proactively detect problems and leverage reasoning to react and dynamically alter a plan. Practical reasoning involves managing conflict resolution where the relevant considerations are provided by the agent's desires about what the agent believes. This involves deliberation by deciding what state of affairs the agent wants to achieve using intentions and by means-end reasoning which is how to achieve those desires using plans. By way of background, an intention is stronger than a desire and planning achieves designated goals. Thus in one embodiment, a basic planning module consists of goals and intentions to be achieved, actions that can be performed, and a representation of the environment. These plans can thus handle priorities, uncertainty and rewards to influence the actual plans. An agent has its own thread of control which promotes the concept of autonomy. Additional information about the capabilities and functionality of agents and distributed multi-agent operating systems, as they relate to our invention, is provided in U.S. patent application Ser. No. 13/250,072, filed on Sep. 30, 2011, which is herein incorporated by reference in its entirety.

Continuing with FIG. 21A, system 2130 is communicatively coupled to patient information 2110 and parameters 2120, and user interface 2140, described below. System 2130 performs processing on patient information 2110 and parameters 2120. In some embodiments, including the practical example described above, system 2130 includes one or more agents 2135, which process patient information 2110 using parameters 2120 to determine goals, plans, patient actions, orders, patient conditions and recommended treatments, or invoke other agents, such as agent solvers, to perform these determinations. In a further example, system 2130 may receive patient data 2111 in the form of a natural language narrative, such as a physician's note, and invoke a data-extraction agent, from solvers library 2122, to extract discrete data from the note. System 2130 may then use the discrete data and content tables 2124 to instantiate and apply another solver agent, from solvers library 2122 to determine a patient's condition and recommended treatments. Finally, upon determining a patient's condition and recommended treatments, system 2130 might invoke an expert rules engine using rules 2121 to determine specific actions to take or a disposition for the patient, based on the determined conditions and recommended treatments.

System 2130 is executed by or resides on one or more processors operable to receive instructions and process them accordingly, in one embodiment, and may be embodied as a single computing device, such as computing device 100 of FIG. 1, or multiple computing devices communicatively coupled to each other. In one embodiment, processing actions performed by system 2130 are distributed among multiple locations such as a local client and one or more remote servers or in one embodiment computing devices at medical organizations 206, 208, and 210 of FIG. 2. In one embodiment, system 2130 resides on a computer, such as a desktop computer, laptop, tablet, or mobile or smart phone computer. Example embodiments of system 2130 reside on a desktop computer, a cloud computer or distributed computing architecture such as platform 212 of FIG. 2, a portable computing device such as a laptop, tablet, ultra-mobile P.C., a mobile phone, or a combination of such devices.

Coupled to system 2130 is a display or user, or user interface, 2140. Display for a user 2140 provides a presentation capability and user interface to facilitate communication with users. Using display for a user 2140, a user may view determined results about a patient or provide additional information such as patient information, in one embodiment. Display for a user 2140 may be a single device or a combination of devices and may be stationary or mobile. In some embodiments, a user interface on display device takes the forms of one or more presentation components such as a monitor, computing screen, projection device, or other hardware for displaying output. In some embodiments, a user interface on display device takes the form of one or more presentation components with user input components, such as a remote computer, a desktop computer, laptop, PDA, mobile phone, ultra-mobile PC, computerized physician's clipboard, or similar device. In some embodiments, data elements and other information may be received from display device by a user 140. Queries may be performed by users through user interface 2140; additional orders, tests, feedback or other information may be provided through the display device to user through user interface 2140.

Environment 2100 includes data store 2110 which includes patient information and data store 2120 which includes parameters. In some embodiments, data stores 2110 and 2120 comprise networked storage or distributed storage including storage on servers located in the cloud. Thus, it is contemplated that for some embodiments, the information stored in data stores 2110 or 2120 is not stored in the same physical location. For example, in one embodiment, one part of data store 2110 includes one or more USB thumb drives or similar portable data storage media. In one embodiment, data stores 2110 and 2120 are distributed at multiple locations including locations of a plurality of medical organizations 206, 208, and 210 or FIG. 2. Additionally, information stored in data stores 2110 and 2120 can be searched, queried or analyzed using system 2130 or user interface 2140, which is further described below.

Data store 2110 comprises information specific to a patient, which in some instances includes incomplete, outdated, uncertain, overlapping, and conflicting information. Moreover, the information might come from a variety of sources and/or exist in a variety of formats including for example, narratives and discretized data. Examples of sources can include patient data from different medical organizations 206, 208 and 210 of FIG. 2, traditional hospitals, walk-in clinics, urgent care facilities, other locations that render medical services, as well as in-home patient monitors and patient-wearable sensors or monitors. In one embodiment, patient information includes one or more of patient data 2111, patient records 2112, previously determined analysis or disposition 2113, which are associated with the patient, recommended treatments 2115, previously determined patient conditions 2116, and past actions 2118 performed for the patient. In some embodiments, patient data 2111 can include lab results, real time or near real time information such as data provided by a physician, including information based on observation or a patient's explanation, information provided by a sensor (for example, blood pressure or heart rate), or other patient data. In some embodiments, patient records 2112 can include electronic medical records ("EMR"), health information exchange ("HIE"), personal health record ("PHR"), patient claims, and other health records associated with a patient.

Previously determined analysis and dispositions 2113 include information relating to previous analyses performed on a patient and previous dispositions determined for the patient, including previous analyses and dispositions determined by way of the multi-agent system, in some embodiments. Multiple-agent system 2130 may handle a complex problem, such as determining patient conditions or recommended treatments. Each of the agents 2135 may generate multiple analyses and/or disposition for the patient. For example, as described above, agents operating in parallel and using different input parameters 2120, and in some instances different patient information 2110, may determine a patient's likelihood of having sepsis (or another condition). In some embodiments, a degree of statistical certainty about a determined disposition of analysis may be arrived at by correlating or otherwise comparing each of the separate analyses and/or dispositions. More specifically, if separate agents 2135 each determine substantially the same analysis or disposition using different levels of patient information, then there may be a higher degree of confidence that the analysis or disposition is accurate, given the available patient information. In some embodiments, if the analysis or disposition of the separate agents ends up being a false positive for detection of a condition, then those agents can be designated or otherwise associated as having less effective determination capabilities. Similarly, where agents are more effective (i.e., more accurate and/or more efficient, such as agents able to perform in less time or with less input information) at detecting a patient's condition, then those agents can be designated or otherwise associated as having more effective capabilities. In some embodiments, the most effective agent may be swapped into (or invoked for) the condition detection process. For example, in determining a patient's likelihood of having sepsis, the most effective agent may be invoked. In some embodiments, it is conceivable that performance or effective capability of an agent may be dependent on the specific patient information 2110. For example, in circumstances where a set A of patient information 2110 is available, agent A-prime may have the best performance, but where patient information 2110 is different, such as if a set B of information is available, then agent A-prime is less effective. But another agent, such as agent B-prime, may be more effective. Therefore, an association can be established of which agent is more effective, based on the specific patient information 2110 that is available. In one embodiment, another agent handles this association and invokes the most capable agent based on the available patient information 2110. In another embodiment, this association is encoded as a logic rule or rules engine. In this way, system 2130 learns and also adapts to be more effective, based on the circumstances (such as the available patient information 2110). In some embodiments, feedback information is provided to a user or health care provider as to which agent or which patient information 2110 and/or parameters 2120 provide the most accurate determination. This feedback information enables health care providers to streamline care for future patients. For example, if the feedback information indicates that a high probability of detection of a condition, such as sepsis, can be determined based on variables V1 and V2 alone, where the range of variable V1 should be RX-RY for a certain patient type and within a specified time window, and the threshold of variable V2 should be T1, and that variables V3-V5 are unnecessary, then accordingly the health care provider only needs to provide information of variables V1 and V2 and might be able to ignore variables V3-V5. In some embodiments, a health care provider might suggest a set of ranges or thresholds for variables (as parameters 2120) or a range or threshold that is different from what is typically used. After agents using the different ranges of thresholds complete analyses, such as determining likelihood of sepsis, system 2130 can provide information to the health care provider, via user interface 2140, for example, as to whether the suggested ranges or thresholds were more effective or less effective at diagnosing the patient's condition.

Recommended treatments 2115 include currently and previously recommended treatments for a patient. In one embodiment, this information includes time-related or near real-time data associated with the time that the recommended treatment was determined, as well as an indication of whether the recommended treatment has been acted upon. In one embodiment, recommended treatments 2115 also specify how the recommended treatment was determined, including for example, available patient information, the type of solver that was applied, and the resulting patient conditions, thereby enabling a health care provider to query the recommended treatments to see how a particular treatment was determined or to generate a report.

Past actions 2118 include previous actions determined by the multi-agent system 2130. Similarly to what is described above in connection to recommended treatments 2115, past actions 2118 may include time information associated with the time that the action was determined or executed, or may also specify how the action was determined or executed.

Data store 2120 comprises parameters and information associated with the multi-agent system 2130. Although depicted as working with a multi-agent system, in one embodiment, data store 2120 works with single-agent system parameters and information, or non-agent system parameters and information. In one embodiment, data store 2120 includes rules for a rules engine 2121, and solvers library 2122. Rules for a rules engine 2121 include a set of rules or library of rules. In one embodiment, rules 2121 are usable by an expert rules engine, such as an agent 2135 in multi-agent system 2130. Alternatively, in a non-agent embodiment, rules 2121 include a library of rules usable by non-agent processes. One example application of rules 2121 by a rules engine includes determining actions or dispositions associated with a patient from a number of determined conditions or recommended treatments.

Solvers library 2122 includes one or more solvers, which can include non-agent solvers, agent solvers (discussed below) or both. In some embodiments, solvers, which may also be referred to as "resolvers," are applied to determine one or more conditions or recommended treatments for a patient. A finite state machine solver may be used to determine the conditions and recommended treatments of a patient suffering from a number of conditions including congestive heart failure. Solvers may also invoke or apply other solvers. Continuing this example, the finite state machine agent solver may invoke a linear solver, such as a mixed integer linear solver, to evaluate each state in order to determine the patient's condition. In one embodiment, the finite state machine returns the actual state for each clinical condition of the patient, which is then passed on to the mixed integer linear solver as parameters, to apply the mixed integer solver based on the clinical state, and content tables 2124. The solvers library 2122 can be updated as new solvers are available. Another example solver is the data-extraction solver, which is described in further detail below. A data-extraction solver is a type of solver that is applied to unprocessed patient information, such as a physician's narrative or patient results data, in order to generate discretized data that is usable for other solvers.

In some embodiments, agents 2135 facilitate solving problems including the problems described above by employing one or more solvers from solvers library 2122. Furthermore, where existing rule systems may utilize forward chaining, backward chaining and combination, agents 2135 can integrate these rule capabilities as well as other traditional and heuristic techniques. These agents 2135, which may be referred to as agent solvers, can also leverage the best techniques for the problem at hand. They can register their abilities to the overall system and coordinate and communicate with other agents, users, or the overall system, to solve problems based on their current capabilities. Still further and as described above in the sepsis-detection examples, new or improved solvers, which may be introduced at future times, are able to be leveraged by swapping out current agents with new agents dynamically and without the need to recompile or reconfigure the system. Thus embodiments using multi-agent system 2130 can provide advantages, in some scenarios, over single-agent systems and non-agent systems. By analogy, a single celled organism is analogous to a single-agent system, while a complex multi-celled organism is analogous to the multi-agent system. Accordingly, the "reasoning" capabilities of multi-agent system 2130 are superior to the "reasoning" exhibited by a single-agent system, and the multi-agent system 2130 is not constrained at design time and has the ability to grow and adapt over time based on future needs not anticipated at the time of instantiation or design.

In some embodiments, agents 2135 provide enhanced decision support by using multi-agent properties like collaboration, persistence, mobility and distributed operation, autonomy, adaptability, knowledge and intelligence, reactive and proactive capability, reuse, scalability, reliability, maintainability, security, fault-tolerance, trust, and other primary properties. In addition, numerous secondary properties of multi-agents in embodiments of our invention may facilitate decision support, including: reasoning, planning and learning capabilities; decentralization; conflict resolution; distributed problem solving; divide-and-conquer strategies for handling complex problems; location transparency; allowing for competing objects to be represented; goal-driven or data-driven including agent-to-agent or user-to-agent; time-driven; support for multiple layers of abstraction above services thereby providing flexibility, adaptability, and reuse and simplification; negotiation; hierarchies having dynamic self-organization; abilities to spawn and destroy agents as needed; utilization of transient and persistent data; abilities to address uncertain, missing or inconsistent data; sensitivity to resource and time constraints; ontology-driven functionality; flexible run time invocation and planning; obligations; ability to act to achieve objectives on behalf of individuals and organizations; organizational influence; and other secondary properties. Examples of agents, which may be used by the multi-agent systems of embodiments of our technologies, include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: Markov decision processing; approximate linear programming; natural language extraction solvers (e.g., nCode); fuzzy-neural networks, logistic and linear regression; forward-chaining inference (e.g., data-driven); backward-chaining inference (e.g., goal-driven); inductive inference; genetic algorithm; neural network including with genetic algorithm for training; stochastic; self-organizing Kohenen map; Q-learning; quasi-Newton; gradient; decision trees; lower/higher bound search; constrain satisfaction; Naives Bayes fuzzy; LP-solver including mixed integer multi-variable min/max solvers; Finite State Machine and HFSM; temporal difference reasoning; data mining for classification, clustering, learning and prediction; K-means; support vector machines; K-nearest neighbor classification; C5.0; a priori; EM, simulated annealing, Tabu search, multi-criteria decision making, evolutionary algorithm, and other similar solvers.

In some embodiments, where particular types of agent solvers are more efficient at handling certain patient scenarios, a planning agent may invoke the particular type of agent solver most appropriate for the scenario. For example, a finite state machine agent solver and a linear solver agent solver may be invoked by a planning agent, in a scenario involving a patient experiencing congestive heart failure. Similarly, a planning agent might invoke one or more agent solvers for determining likelihood of sepsis, based on patient information 2110 available and/or the effective capability of the agent solver(s). In some embodiments, agent solvers invoke other agent solvers as necessary.

Continuing with FIG. 21A, some embodiments of multi-agent system 2130 employ decision making for applications including, for example, searching, logical inference, pattern matching and decomposition. A subset of solvers library 2122 includes decision-processing solvers 2123. Decision processing solvers 2123 are a special set of solvers used for decision making, although it is contemplated that in some embodiments any solvers of solvers library 2122 or solver agent maybe used for decision processing. Examples of agent decision procession applications include: searching, including heuristic and traditional searching; list; constraint satisfaction; heuristic informed; hill climbing; decision tree; simulated annealing; graph search; A* search; genetic algorithm; evolutionary algorithm; Tabu search; logical inference; fuzzy logic; forward and backward-chaining rules; multi-criteria decision making; procedural; inductive inference; pattern recognition; neural fuzzy network; speech recognition; natural language processing; decomposition; divide-and-conquer; goal tree and subgoal tree; state machine; function decomposition; pattern decomposition; and other decision-processing applications. In some embodiments, agents designed or instantiated with a particular decision-processing application may be swapped out, in a more seamless and transparent manner than with non-agent systems, with another agent having more advanced decision processing functionality as this becomes available or is needed.

Solver content-parameters 2124, which is also referred to as "content tables" 2124, include parameters used for instantiating and applying the solvers. Content tables 2124 provide parameters that specify information regarding conditions, drugs, contra-indications, treatments, orders or other actions, and other parameters used in conjunction with patient information to determine conditions and recommended treatments. In one embodiment, content parameters 2124 are formatted as independent tables, which might take the form of a matrix, which can be maintained, updated, or swapped out with other tables, by health care providers, physicians, or experts independent of patients. For example, a content table may specify parameters relating to diabetes including what factors in patient information indicate that the patient is in hypoglycemia, what factors in patient information indicate that the patient is in hyperglycemia, contra-indications, treatments such as drugs and drug dosages that should be administered, or additional testing that should be ordered. In another example, content tables specify the set(s), range(s), and/or threshold(s) of variables for detecting likelihood of a condition, such as sepsis. In some embodiments, rows of a content table correspond to different sets, ranges, or thresholds of variables such that a first agent can perform its analysis using content specified in a first row A, and a second agent working in parallel (or the first agent at a later time) can perform its analysis using content from a row B. Further, in some embodiments, the results of analyses can be entered into the rows or associated with the rows. Thus, where multiple agents are running analyses in parallel, with each agent using a different set of parameters specified in one row, the results of the row that correspond to the most effective analysis may be provided to the health care provider or otherwise published to the outside world as the result of the determination for whether the patient has the condition, even though in fact there may be multiple separate results from the different analyses, in some embodiments. This is because in many instances, the health care provider only desires to know whether the patient has a particular condition, and doesn't care about a bunch of different agent-generated results coming from diverse parameters 2120, some of which are more accurate and some of which are better than others.

In some embodiments, content tables 2124 and patient information 2110 provide the information necessary for a solver to determine patient conditions and recommended treatments. Content tables may be updated independently, as new information, treatments, or drugs become available.

Goals 2126 include objectives which guide the system, such as embodiments of a multi-agent, single-agent, or non-agent system 2130, in the selection of a plan and, ultimately, the determination of what actions to take place as a result of incoming patient data. Therefore in some embodiments, goals are based on incoming patient information. For example, a goal may specify "determine if patient has sepsis," "manage conditions for sepsis," "manage conditions for sepsis while keeping other patient conditions stable," or "minimize the cost of patient treatment." In some embodiments, goals are used to motivate agents 2135. Specifically, agents 2135 operate under guidance of a goal that is consistent with patient information when deciding what actions to take, plans to select and execute, or which solvers to invoke. Thus, any plan selected and executed will be consistent with the determined goals 2126, which are based on patient information 2110. Moreover, as patient information 2110 changes, such as when newer or additional patient information 2110 becomes available or a patient's condition changes during the course of treatment, goals 2126 may be changed or replaced. In some embodiments such as multi-agent systems operating under the belief-desire-intention ("BDI") model, a goal is analogous to a desire. Accordingly, in one embodiment, agents 2135 may act to fulfill a desire that is based from a set of agent beliefs or facts determined from available patient information 2110. In some embodiments, goals 2126 can be organized in one or more sets, groups, tables, databases, or libraries with, in some embodiments, subgroups related to similar goal-objectives; for example, a subgroup of goals may relate to handling patient treatment costs or treating cancer.

Plans 2128 include, in some embodiments, specific executable algorithms, instructions, schedules, or the similar plans for carrying out a specific objective that is consistent with a determined goal 2126. Alternatively in other embodiments, plans 2128 may specify intention or an intended outcome to be achieved that is consistent with a determined goal 2126. Plans 1228 can include sets or libraries of plans, which in some embodiments are associated with certain goals 2126. For example, for the goal of "manage conditions for sepsis while keeping other patient conditions stable," plans associated with this goal may specify actions for determining a patient's condition by examining patient information including blood pressure and blood oxygen. The plan may further specify recommended treatments, orders, or other plans to be executed. In some embodiments, plans 2128 also include planning agents, which can assist in the selection and execution of a plan. For example, a planning agent may select a plan, which in some embodiments may also be an agent, for treating sepsis based on patient information that indicates sepsis; the plan may specify using solvers such as logistical regression on the patient information to determine the patient's condition and recommended treatment, in one embodiment.

In another example, a specific plan under the sepsis-detection goal, may specify using a data-extraction agent for extracting discrete data items from a physician's note written in natural language, and then instantiating one or more solver agents, which carry out the processes for determining likelihood of sepsis, described herein including the embodiment described in connection to FIGS. 9A and 9B, to determine the patient's conditions and recommended treatments. In one embodiment rather than specifying a specific solver or set of solvers to use (e.g., data-extraction and finite state machine solvers), a plan may specify an intention, (e.g., determine patient's condition when patient information indicates sepsis), and invoke an agent 2135 to select the best solver applicable based on the available patient information 2110. Under the BDI model, a plan is analogous to an intention; thus a plan is sort of like an intention to process the goal with which the plan is associated. The plan 2128 is executed to meet the goal 2126, or partially meet the goal. In one embodiment, a planning engine is used for determining plans 2128 consistent with goals 2126. The planning engine, which could be an agent, non-agent rules engine, a decision tree, or other decision process, selects a plan.

Figure 21B:
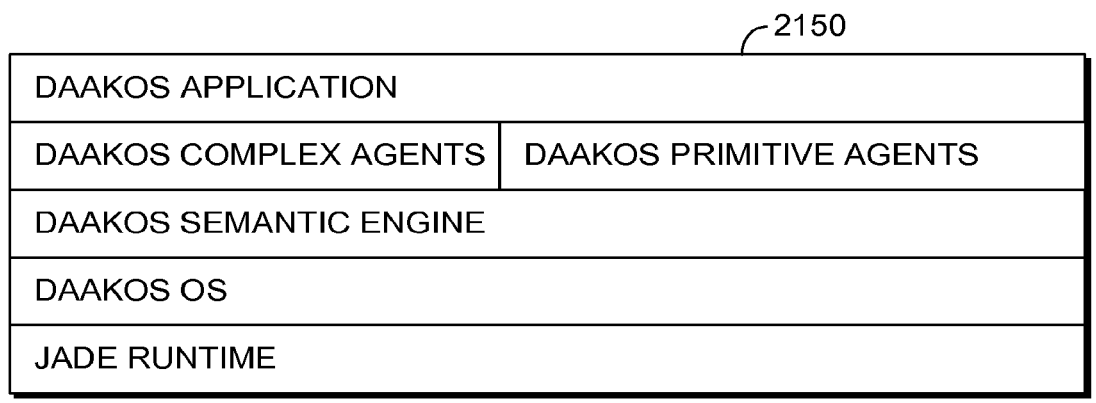
FIG. 21B depicts an exemplary framework of a multi-agent system suitable for implementing an embodiment of the invention.

Turning to FIG. 21B, an illustrative example is provided of a framework suitable for implementing a multi-agent system, such as computer system 2130 of FIG. 21A, and is referenced generally by the number 2150. In some embodiments, framework 2150 is suitable for supporting decision support manager 202 of FIG. 2. In some embodiments, decision support manager 202 is built on framework 2150, and in some embodiments manager 202's services such as identify management 214 and multi-risk assessment 216 operate as software services on framework 2150. Furthermore, in some embodiments using multi-agent computer system 2130, services 214 and 216 are carried out using one or more agents.

As shown in FIG. 21B, framework 2150 has a layered architecture. At the lowest level depicted in the embodiment shown in FIG. 21B, framework 2150 includes a layer for JADE runtime. In other embodiments, frameworks such as Cougaar, Zeus, FIPA-OS, or an open-agent architecture, may be used. Although not a requirement, it is preferable that the framework include the following properties, which are present in the JADE framework: FIPA compliance; support for autonomous and proactive agents and loosely coupled agents; peer-to-peer communication; fully distributed architecture; efficient transportation of asynchronous messages; support for white and yellow page directory services; agent life-cycle management; agent mobility; subscription mechanism for agents; graphical tools for debugging and maintenance; support for ontology and content languages; library for interaction protocol; extensible kernel for extensions to build customized framework; in-process interface for launching and control; support for running agents on wireless mobile devices; integration with various Web-based technologies; and pure Java implementation.

JADE, which is an acronym for Java Agent DEvelopment framework is a middleware software development framework that is used for facilitating implementation of multi-agent systems. Specifically, the JADE platform includes functionality which facilitates the coordination of multiple agents, and functionality for facilitating the distribution of agent platforms across multiple machines, including machines running different operating systems. Moreover, JADE further includes functionality for changing system configuration at run time by moving agents from one machine to another, as required.

Continuing with FIG. 21B, on top of the JADE runtime framework is the Distributed Adaptive Agent Knowledge Operating System ("DAAKOS"). DAAKOS is a decision-support framework built upon JADE or another multi-agent framework. DAAKOS is a multi-agent framework with heuristic, adaptive, self-optimizing and learning capabilities and the ability to decompose complex problems into manageable tasks to assist clinical decision making at point of care. For example, caregivers and other users can leverage this intelligent agent system to detect a change in personal health or to leverage up to date knowledge about medical conditions, preventive care, and other relevant interests. Accordingly, in one embodiment, DAAKOS can be thought of as an intelligent, self-learning agent system using a cloud metaphor.

Specifically, DAAKOS utilizes multi-agents 2135 that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. In some embodiments, intelligence is achieved within agents by way of support provided by a rich ontology within a semantic network. For example, a multilevel of collaborating agents 2135 allows low-level agents to transform data so that it can be passed on to another agent, and to continue the data transformation until the data has been completely transformed from bits of data which may sometimes represent incomplete, outdated, or uncertain data, to form a usable collection of data with rich meaning. In this example, when it becomes necessary to attack complex problems, the agent 2135 is permitted to constrain and narrow its focus at an individual level to support decomposition. Domain specific agents can be leveraged in some embodiments to use an ontology to manage local domain-specific resources.

The DAAKOS operating system layer handles process management, scheduling, memory, resource management, Input/Output ("I/O"), security, planning, as well as other processes traditionally handled by operating systems, and in some embodiments includes memory, which may include short, intermediate, and/or long-term memory, I/O, internal agent blackboard, context switching, kernel, swapper, device resource management, system services, pager, process managers, and logging, auditing, and debugging processes. In some embodiments, the DAAKOS operating system layer is a distributed virtual operating system. On top of the DAAKOS operating system layer, in the embodiment illustratively provided in FIG. 21B, is the DAAKOS Semantic Engine, which provides the platform for DAAKOS agents 2135. DAAKOS agents 2135 include complex agents and primitive agents. On top of the agents' layers are DAAKOS Applications. These include, for example, DAAKOS agent solvers such as a finite state machine instantiated and executed to determine a patient's conditions and recommended treatments, transactions knowledge engines, and other applications leveraging DAAKOS agents 2135.

Now turning back to FIG. 2, in one aspect, the cloud-computing platform 212 can communicate internally through connections dynamically made between the virtual machines and computing devices and externally through a physical network topology to resources of a remote network such as with medical organizations 206, 208, and 210. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As further shown in FIG. 2 with references to FIGS. 21A and 21B, multi-site decision support manager 202 is capable of communicating with a number of different entities or medical organizations, such as a hospital 206, a physician's office 208, and urgent care clinic 210, for example, for the collection of patient information, such as patient information 2110 of FIG. 21A, from a number of individual entities. Patient information 2110 collected from different entities may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information. Additional examples of patient information 2110 is provided in connection to FIG. 21A.

It should be noted that the medical organizations shown as communicating with multi-site decision support manager 202 in FIG. 2 are provided by way of example only and are not intended to limit the scope of the present invention in any way. Each medical organization may have one or more computing devices such as computing device 100 of FIG. 1, for communicating with the decision support manager 202. It will be appreciated that each medical organization is an organization for treating patients such as a hospital, urgent care clinic, physician's office, emergency department, and the like. Each medical organization maintains its own enterprise healthcare system and each organization is not directly connected with one another such that separate medical record systems are utilized by each medical organization. The medical organizations send information to the cloud-computing platform 212 and not typically directly between one another. In addition, communication between the manager 202 and the various medical organizations may be via one or more networks, which may comprise one or more wide area networks (WANs) and one or more local area networks (LANs), as well as one or more public networks, such as the Internet, and one or more private networks.

Further, medical organizations may be able to access the manager 202 in a variety of ways within the scope of the present invention. For example, in some embodiments, a medical organization may have a native clinical computing system, which may be able to communicate with the manager 202. In other embodiments, a client application associated with the manager 202 may reside or partially reside on one or more of the medical organization's computing devices facilitating communication with manager 202. In further embodiments, communication may simply be a Web-based communication, using, for example, a Web browser to communicate to the manager 202 via the Internet. Any and all such variations are contemplated to be within the scope of embodiments of the present invention.

Manager 202 is available in the cloud-computing platform 212 in a manner that enables the cross-venue recognition of a patient through the use of a patient identity management component 214 such as an Electronic Master Person Index (EMPI). Patient identity management component 214 allows manager 202 to match data for the same patient that originates with different medical organizations. In some embodiments, identify management component is embodied as one or more software services operating on a multi-agent system 2130, wherein processes associated with patient-record matching are carried out by one or more agents. Further examples of such embodiments of identity management component 214 are provided in U.S. Provisional Application No. 61/641,097 filed on May 1, 2012, which is herein incorporated by reference in its entirety.

In embodiments, a processing element of manager 202, which may be embodied as an agent 2135, receives and monitors new information 2110 for an individual patient (from Continuity of Care Documentation (CCD), extracted information HL7 messages) that is sent to the cloud platform 212 to determine whether or not it is appropriate to open a multi-site risk assessment array 216, or assessment 216 which may be embodied as a vector, table, listing, array, or other set of information, for an individual patient for a particular condition. Exemplary conditions for which an array may be opened for a patient include, but are not limited to, sepsis, infection risk (both community and hospital acquired), blood management and anemia care, shock, Venous thromboembolism (VTE), heart failure, asthma, renal failure/dialysis, wound care, compliance, immunizations, injury patterns, COPD care, controlled substance manipulation, emergent surgical evaluation, travel medicine, dependent care (pediatric and elderly), and system abuse. A sentinel or triggering event may be identified by manager 202 based on information 2110 sent to cloud platform 212 by one or more medical organizations 206, 208, and 210. If a triggering occurs, a transient array for the patient is created.

A state-based array is created that persists or remains active in the cloud platform 212 over a defined period of time, which may be determined based on the nature of clinical utility of the condition or disease represented by the array. An audit trail of time of patient information, medical organization sending patient information, and other information is created and maintained. A persistent assessment 216 offers performance advantage because the information from multiple medical organizations remains together on demand to support a specific decision support objective versus having to perform a query of one medical organization's information at the time the information is needed. In one embodiment, one or more agents 2135 may be used to update an assessment 216, read the assessment, and otherwise access the assessment information that is stored in a database. If implemented, inclusion or exclusion nodes can also be populated at this time.

Manager 202 builds a multi-site risk assessment array 216 for an individual patient. Multi-site risk assessment 216 includes one or more state "nodes," compartments, or state variables, for the individual patient. In some embodiments, including embodiments where assessment 216 is embodied as an array or other data set, each node or state variable in the assessment 216 represents a distinct parameter for a particular condition or patient information. Assessment 216 includes a defined period of persistence based on the nature of the clinical utility of the particular condition. For example, an assessment array for sepsis for the patient may last 48 hours while an assessment array for controlled substance manipulation for the patient may last years.

One or more nodes of the assessment array 216 may be supplemented with additional nodes that are used to influence exclusion or inclusion logic (for example, if glucose levels are state node, it may be necessary to also define an exclusion node that is flipped for diabetic patients, indicating to the evaluation agent that the glucose node should be ignored). In addition, a single patient may have multiple assessment arrays open at the same time. Based on the persistence criteria for each assessment, the number of active assessment arrays for a single patient may be in flux.

It is likely that not all nodes in the system will be populated by each medical organization due to limitations in the electronic health record implementations at each medical organization. For example, if there are 20 nodes, medical organization 1 may only populate nodes 1-5, 7, 12, and 18-20, while medical organization 2 populates nodes 1-6, 8, 14 and 17-20. Collectively medical organizations 1 and 2 would have populated nodes 1-8, 12, 14 and 17-20, creating a more comprehensive view of the patient status than either site was individually able to generate. This allows for gaps in patient information to be filled in across sites and over time.

Population of the status of each node of assessment array 216 is determined from the patient information 2110 received for the individual patient based on logic applied to the information. The logic used may include, but is not limited to, binary findings such as: 1) presence or absence of a clinical finding for the individual patient; 2) presence or absence of a medication for the individual patient; 3) presence or absence of a diagnosis code for the patient; and 4) presence or absence of a social history indicator for the patient. The logic applied to the patient information may also be range-based findings such as: 1) a vital sign for an individual patient being above or below a threshold; 2) a lab result for a patient that is greater than or less than a threshold value; 3) whether a condition of a patient has persisted for longer than an indicated duration; and 4) whether a condition for a patient disappears sooner than an indicated duration. In some embodiments, this logic is carried out by an agent 2135.

The status or visual indicator of each node in assessment array 216 may also vary based on the patient information. Visual indicators of each node are shown in more detail with respect to FIGS. 4-8 and discussed in more detail below. The node status can be: 1) binary (on or off); 2) ranged, such as a sliding scale (e.g., the higher the patient's temperature the darker the color of the node); 3) based on a numerical representation (e.g., number of the patient's temperature); or 4) coded.

A manager 202 monitors the active assessment arrays 216 to determine when the actionable criteria for assessment arrays 216 have been met, and if so, triggers escalation logic. In some embodiments, agents operating in parallel monitor assessment arrays 216 for actionable criteria. Monitoring can be based on, but not limited to: 1) the number of nodes in an on-state; and 2) a calculated value if nodes use numeric state. For example, if there are five nodes, each of which can have a value of 0-3, the escalation logic could be triggered by a total value of five or more. The monitoring can be based on a combination of "on" and calculated values (e.g., three nodes in a "warning" status=equivalent of one node in an active status). In some embodiments, employing multiple agents operating in parallel (or a single agent serially performing what would otherwise be parallel-performed tasks), each agent applies escalation logic on an assessment array 216. In some embodiments, the array 216 will be the same for the agents operating in parallel, and in some embodiments this information will be different, as described above in connection to FIG. 21A. Likewise, escalation logic may be different for different agents. Thus the escalation logic for one agent may be triggered by a total value of 5 or more, whereas the escalation logic for another agent might be triggered by a total value of 8 or more or yet another combination of "on" and calculated values.

In embodiments wherein agents are operating in parallel, to handle situations where some agents are triggered and some are not, one agent may be designated as the standard or baseline, whose results are acted upon, and the others designated as alternatives whose results are recorded and evaluated against the patient's condition and disposition. Where these alternative agents are determined to be more accurate or effective at diagnosing the patient's condition, these agents may be swapped in place of the standard agent or designated as the new standard or baseline, at a later time. In some embodiments, the analysis results from each agent is provided to a user via user interface 2140 and so that the parallel-operating agents can be evaluated. Thus in such embodiments where each parallel-operating agent has a different range(s) or threshold(s) of variables, the user is provided feedback regarding which range(s) or threshold(s) were better.

In some embodiments escalation logic includes logic for receiving input from one or more agents operating in parallel and determining based on the received input when to invoke escalation logic. For example, escalation logic may be invoked only where two or more agents report a trigger, or as another example, where the parallel-operating agents are weighted based on their past performances; escalation logic may be invoked based on combinations of the agents weighting and whether the agent is reporting a trigger. To illustrate this example, consider a scenario where four agents are operating in parallel and one of the agents (agent 1) is weighted more heavily because that agent has repeatedly been shown to be more effective at detecting the patient's condition, agents 2-4 are weighted less. Escalation logic may be invoked if agent 1 reports a trigger but agents 2-4 do not report a trigger, because agent 1 is weighed more heavily. On the other hand, escalation logic may be invoked where agents 2-4 report triggers but agent 1 does not. In these embodiments, a separate agent may handle escalation logic and receive reporting from the parallel-operating agents. In some embodiments, escalation logic may be carried out with an agent or rules engine.

Manager 202 can escalate based on escalation logic implemented in a number of manners. These include but are not limited to active escalation methods including: 1) sending an alert to the primary provider on record for that patient; 2) sending an alert to all providers with documented patient contact during the window of activity for the matrix; and 3) sending an alert to the patient encouraging the patient to take further action by returning to the patient's provider or going to the emergency department. Reactive escalation may include modifying the system behavior due to the status of the patient's array, based upon the next patient event (such as admission, new order, opening patient's chart). Modifications of system behavior can include: 1) visually flagging the patient in the system; 2) proactively assembling previous records for immediate review at time of next admission; and 3) recommending a care plan to the provider currently interacting with the system.

Upon conclusion of the persistence period defined for the specific assessment array 216, the status of the array is changed to "closed." This will retain the information for audit trail purposes, while preventing it from inappropriately interjecting into subsequent episodes of care.

Figure 3:
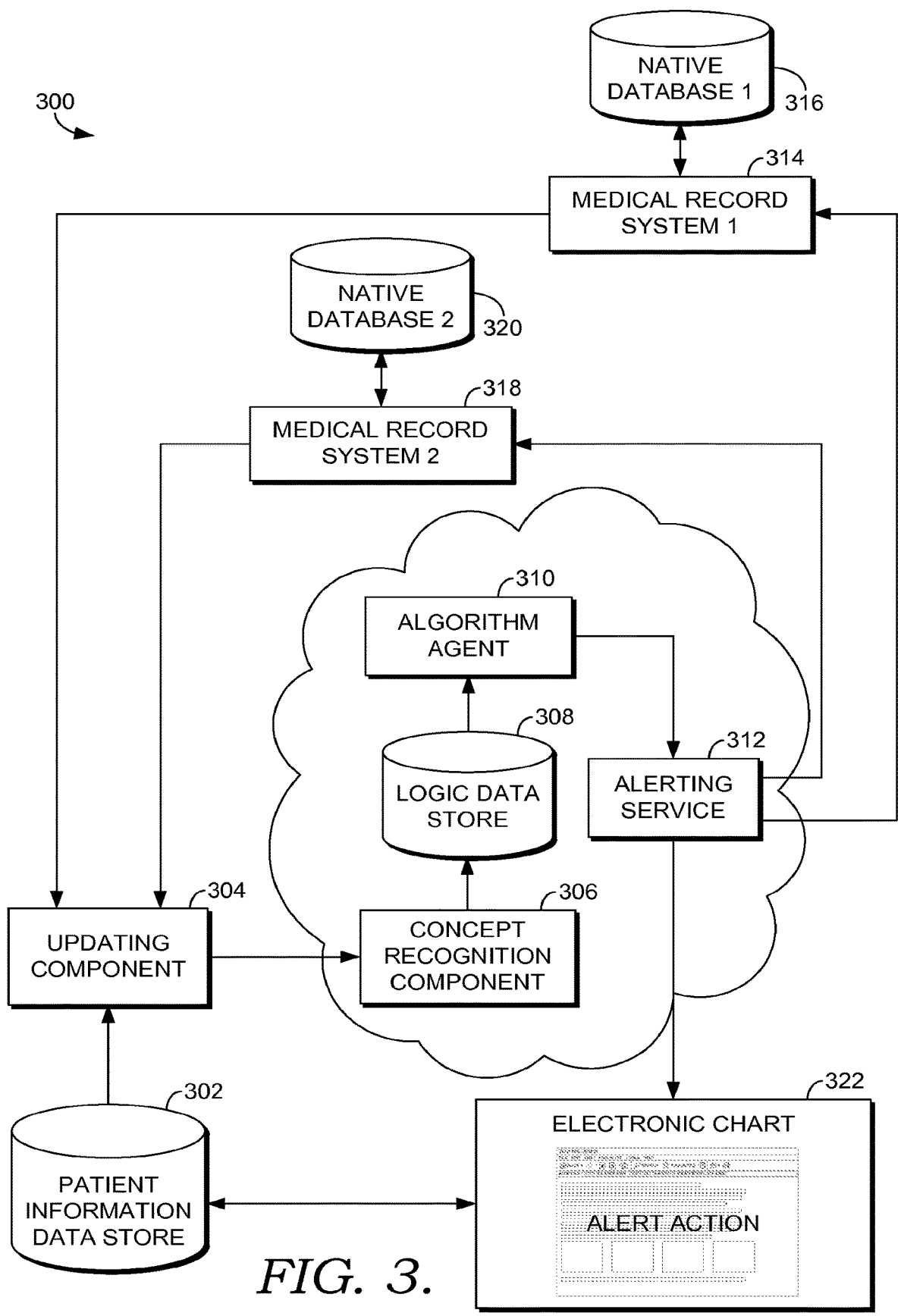
FIG. 3 is a block diagram of an exemplary system for enabling multi-site surveillance and decision support for a patient's medical care, in accordance with an embodiment of the present invention.
Figure 4:
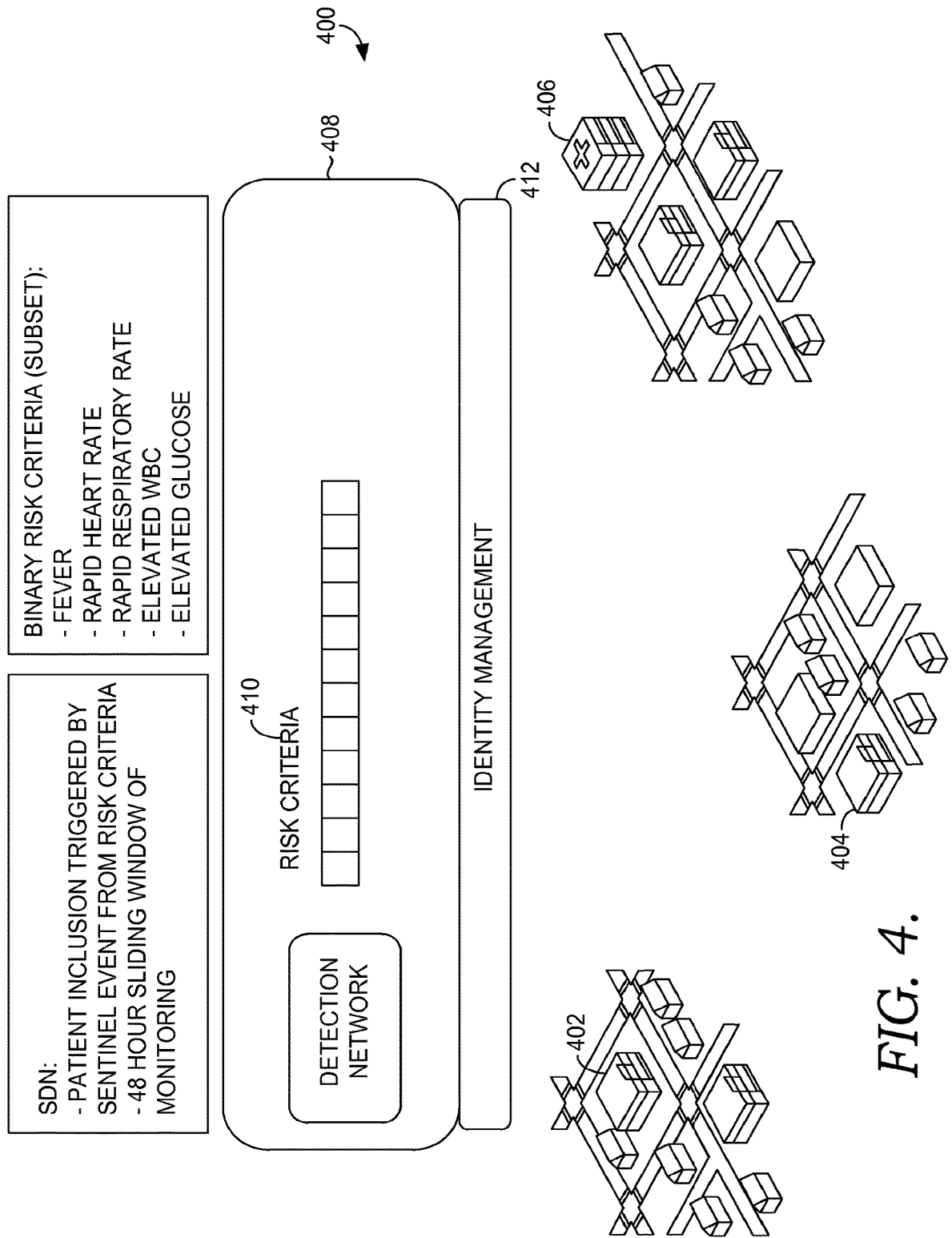
FIGS. 4-8 are diagrams showing multi-site decision support, in accordance with embodiments of the present invention.

Turning now to FIG. 3, with continuing reference to FIGS. 21A and 21B, a block diagram of an exemplary system 300 is shown for enabling multi-site surveillance and decision support for a patient's medical care, in accordance with an embodiment of the present invention. Initially, a patient information data store 302 is illustrated that stores information including patient records, such as electronic medical records (EMR) that can be accessed by various applications. For instance, a particular patient's EMR may be accessed by one or more providers associated with different medical organizations. In some embodiments, data store 302 includes the data store of patient information 2110 of FIG. 21A. Further, in some embodiments, a patient's EMR may not be accessed by a particular provider at a particular medical organization, but may be populated by patient information received from that provider at the medical organization. For example, multiple medical organizations, including hospitals, clinics, doctors' offices, etc., may treat the same patient at some point in time, but may not share a common medical record system, and thus may not all have access to the patient's EMR. Instead, these medical organizations may send patient information to a location that stores the patient's EMR so that this information can be populated into the EMR. This patient information may also be monitored and used to determine whether the patient is at risk of developing a particular disease or condition.

The patient information can be returned by one of several methods. For instance, the updating component 304, in one embodiment, acts as a crawler and actually reaches into another medical organization's medial record system to pull relevant information for a particular patient who is being monitored or who may be monitored in the future for being at risk for a particular disease or condition. In some embodiments, functions of updating component 304 are facilitated by one or more agents 2135. The updating component 304, similarly, may query the medical organizations medical record system to obtain this patient information. Using this method, the crawler may include a program or application that tells it exactly what type of information to retrieve. Alternatively, the updating component 304 may not have the capability or permission to crawl for patient information, but may receive patient information such that it is the responsibility of the medical organization treating the patient to send the patient information to the updating component 304. Using either method, the updating component 304 eventually receives patient information. The concept recognition component 306 performs synonymic discovery and is generally responsible for reconciling terms used by the various medical organizations, and in some embodiments is facilitated by one or more agents 2135. For instance, if a first medical organization calls a white blood cell count test WBC and a second medical organization calls the same test WC, the concept recognition component 306 would have this information stored to determine that both terms are referring to the same test. In some instances, the concept recognition component 306 reconciles the test results themselves, such as if two different medical organizations use a different measuring system. In some embodiments, concept recognition component 306 is embodied as one or more software services operating on multi-agent system 2130. Additional information about the capabilities and functionality of such embodiments as they relate to our invention is provided in U.S. Patent Application No. 61/521,219, filed on Aug. 8, 2011, which is herein incorporated by reference in its entirety.

The logic data store 308 stores logic that is used to determine when a patient is at risk for a particular disease or condition and when it is the appropriate time to alert one or more medical organizations, the patient, the primary care provider, etc., that the patient is at risk based on the patient information received from the multiple medical organizations. In some embodiments, logic data store 308 includes one or more components of parameters 2120, such as solvers library 2122, rules 2121, and or content tables 2124. In one embodiment, the logic data store stores arrays (which can be embodied as arrays or sets of information about a patient such as tables, listings, relational data bases, pointers, or similar information, and further in some embodiments may be empty where specific patient information is unavailable) including that will be discussed in more detail in references to FIGS. 4-8 below. "Arrays" as used herein, are a management system for monitoring the symptoms that a user has in reference to a particular disease or condition. This information, together, is called an array. In some embodiments, some boxes of an array may have patient information and some may not, indicating that patient information corresponding to the blank boxes has not yet been received from the medical organizations. It should be noted that arrays can have duration of time in which they remain active. This duration of time is dependent, at least in part, on the disease or condition that is being monitored in relation to the patient. For instance, an array for monitoring a patient's risk of sepsis may be active for 24-48 hours, or even up to 72 hours. An array for substance abuse, on the other hand, may be active for several years. The duration of an array may be nonmodifiable, or may be modifiable by a medical organization, the primary care physician, or the system that monitors the patient's risk for a particular disease or condition. The concept recognition component 306 may communicate patient identifying information to the logic data store 308, including an identification of the patient.

Algorithm agent 310 is responsible for executing algorithms or logic, such as the logic stored in the logic data store

308. In some embodiments, algorithm agent is an agent 2135, which may be a solver agent or an agent that invokes other solver agents. Algorithms or logic may comprise algorithms and/or logic from solvers library 2122, rules 2121, and or content tables 2124, in some embodiments, and further may be handled by one or more dedicated agents. The algorithms or logic determines when, based on an array, a patient is at risk for developing a particular disease or condition. Exemplary logic is further discussed in relation to FIGS. 9A and 9B. Algorithm agent 310 may additionally be responsible for updating the logic based on results of patient monitoring. For example, in embodiments wherein multiple agents are invoked to determine when a patient is at risk for developing a particular condition, agent 310 may swap out less-effective agents or agent 310 may facilitate updating the logic to indicate which particular agent should be used or which variable range(s) or threshold(s) should be used, based on the analysis results of the parallel-operating agents.

In some embodiments, algorithm agent 310 may include a multi-agent system that may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities, and choices that communicate via declarative messaging and use abstractions to allow for future adaptations and flexibility. An agent has its own thread of control, which promotes the concept of autonomy. For example, the multi-agent system may have knowledge as to whether patients for which alerts are sent are actually diagnosed with the disease or condition for which they are being monitored. If the percentage is low or otherwise unacceptable as to the patients being diagnosed, the criteria for being at risk for that disease or condition may be altered such that alerts and notifications are sent when a different set of criteria is met. Further, the individual medical organizations may have individual criteria that they use to determine when a patient is at risk, and thus when it would like to receive an alert from the monitoring system. An algorithm agent 310 (or a plurality of agents 310) may monitor this information to determine when it is appropriate to alert, notify, etc., one or more medical organizations or other parties involved in the medical care of the patient. For instance, each provider with document-patient contact during a period of time that the active risk assessment array has been active may be notified, in one embodiment.

The alerting service 312 receives input from algorithm agent 310 as to when and whom to alert. In an alternative embodiment, the alerting service 312 is responsible for using inputs from the algorithm agent 310 to determine when and whom to alert. The alerting service 312 may comprise one or more rules that allow the alerting service 312 how to determine when to communicate an alert, notification, etc. In one embodiment, each medical organization that has provided patient information to the monitoring system receives an alert when the criteria are met for the patient being at risk for a particular disease or condition. Further, the patient may be alerted via a text message, a telephone call, a letter, an e-mail, etc., so that the patient can initiate a follow-up appointment with the primary care physician or another provider. Even further, the primary care physician, while he or she may not have provided any patient information that was used in the array to determine that the patient is at risk for a particular disease or condition, may be alerted. In some embodiments, the notification or alert is recorded in an electronic chart 322 corresponding to the patient, such as an EMR so that it can be used for future reference by other clinicians.

While in some embodiments, the monitoring system establishes the criteria for determining whether a patient is at risk for a particular disease or condition, in another embodiment, each medical organization may use different criteria for determining whether a patient is at risk for a particular disease or condition. For instance, a first medical organization may use a heart rate criteria of above 95 beats per minute (bpm) for a patient being at risk for developing sepsis. A second medical organization may use a heart rate criteria of above 98 bpm for a patient being at risk for developing sepsis. When a patient's heart rate is at 96 bpm and other criteria are met for being at risk for developing sepsis, the first medical organization may receive an alert, but the second medical organization may not receive an alert, in some embodiments. In these embodiments, the second medical organization may receive a notification indicating that the first medical organization received an alert based on its criteria for sepsis. This may prompt the second medical organization to take a closer look at the patient's medical information to determine whether it needs to take action. While there are many different ways of implementing an alerting service 312, the previous examples are provided as illustrations as to how the alerts and notifications may operate and do not limit embodiments of the present invention. Other scenarios not specifically mentioned here are contemplated to be within the scope of the present invention.

As shown, alerting service 312 can alert the medical organizations by communicating an alert to the medical record system used by each medical organization. For instance, the first medical organization may utilize medical record system 1 (item 314), which has a native database 1 (item 316) that stores patient information including EMRs for each of the medical organizations with which it operates. The alert may be communicated to medical record system 1 (item 314), and then the alert is sent to the particular medical organization or clinician within that medical organization. Similarly, the alert may be communicated to medical record system 2 (item 318), which has a native database 2 (item 320) for storing patient information including EMRs for each of the medical organizations with which it operates. The alert may appear on the patient's EMR, or may be sent directly to the clinician responsible for treating the patient. As shown in FIG. 3, the medical record systems send patient information to the updating component 304. This patient information is the patient information used to populate the arrays to determine whether a patient is at risk for a particular disease or condition. While the patient information comes from individual medical organizations, each medical organization may utilize a particular medical record system, and thus when the practitioner enters patient information into the patient's EMR at the medical organization (e.g., hospital, urgent care, doctor's office), the patient information is sent to the medical record system where it is stored. The alert sent from the alerting service 312 may take many forms, including, for exemplary purposes only and not limitation, an email, text message, telephone call, pager message, fax, or the like. Even further, the alert may comprise a recommended care plan for the provider based on the patient information received.

As shown in the embodiment of FIG. 3, the concept recognition component 306, the logic data store 308, the algorithm agent 310, and the alerting service 312 are in the cloud. In some embodiments these components, services, and data store are implemented on cloud-computing platform 212 of FIG. 2. As mentioned, cloud computing generally refers to a way for on-demand network access to a shared pool of configurable computing resources, including, for instance, networks, servers, storage, applications, or services. As such, the components listed above in the cloud are accessible by way of the Internet or other network. While these components are shown in the cloud, other components may also be in the cloud, although not shown in FIG. 3.

Figure 5:
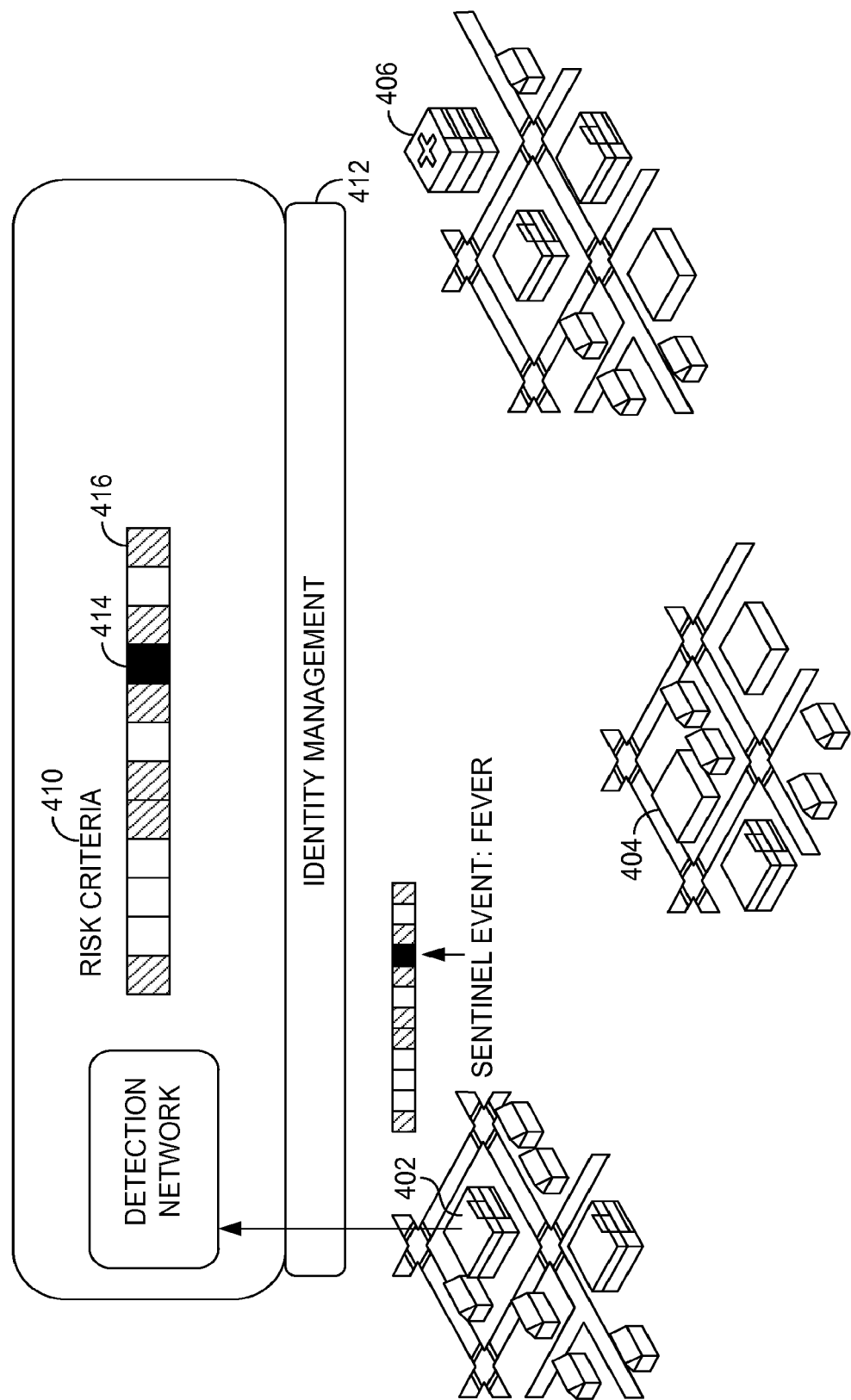

Referring now to FIGS. 4-8, an example 400 of monitoring patient data from multiple organizations for decision support is shown. Three organizations, a physician's office 402, urgent care clinic 404 and emergency room of a hospital 406, are sending patient information to manager 408 (also manager 202 of FIG. 2). An identity management component 412 (such as 214 of FIG. 2) identifies the patient information so that it can be correlated with information for the same patient from other organizations or sources. In this example, there are multiple risk criteria for a sepsis array including: fever, rapid heart rate, rapid respiratory rate, elevated white blood cells, and elevated glucose. The sepsis array is triggered by satisfaction of one of the risk criteria and is set to persist in a cloud computing environment for 48 hours. With reference to FIG. 5, the sentinel event of a fever 414 occurs and is reported by the patient's physician's office 402 to the manager 408. The elevated fever 414 satisfies one of the risk criteria and a sepsis array 410 is opened for the patient. Gray boxes, such as box 416, indicate boxes or nodes that have patient information that has been received from one or more of the medical organizations and has been populated into the array.

As shown in FIG. 5, risk criteria 410 may be dark boxes that are satisfied risk criteria, such as box 414, gray boxes that are criteria reported by that particular organization (in this case the physician's office), such as box 416, and white boxes represent criteria that are not reported by the particular organization. It will be appreciated that satisfied criteria, reported but not satisfied criteria and not reported criteria may be identified in any variety of manners including by colors (red, green, and white) or other visual representations.

Figure 6:
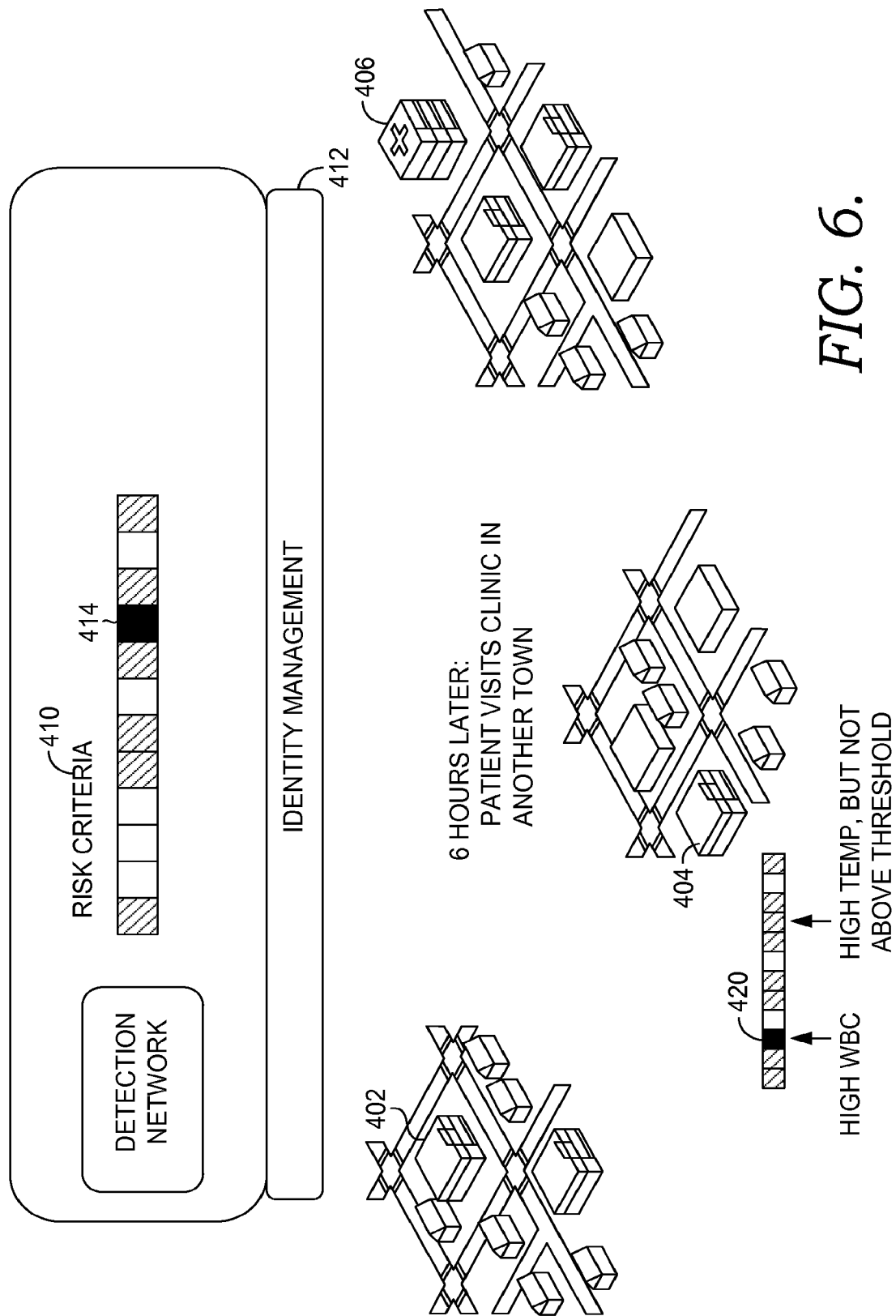
Figure 7:
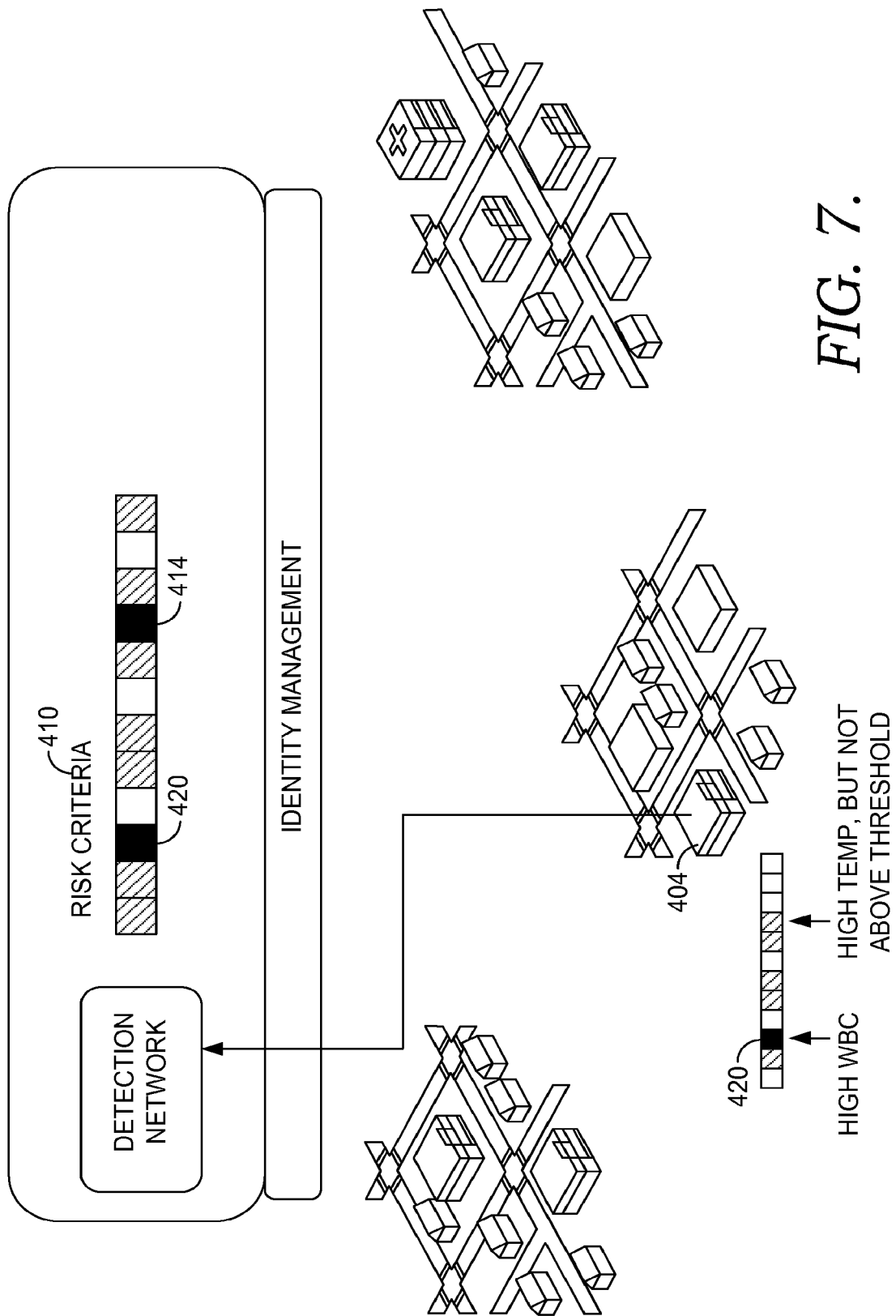

With reference to FIGS. 6 and 7, six hours later while visiting urgent care clinic 404 across town, which is separate from and not connected to the physician's office 402, the urgent care clinic 404 sends patient information to the manager 408 indicating that the patient has a high white blood cell count 420. This information is populated by the manager 408 into the sepsis array 410 already existing for the patient based on the patient's previous visit to physician's office 402.

Figure 8:
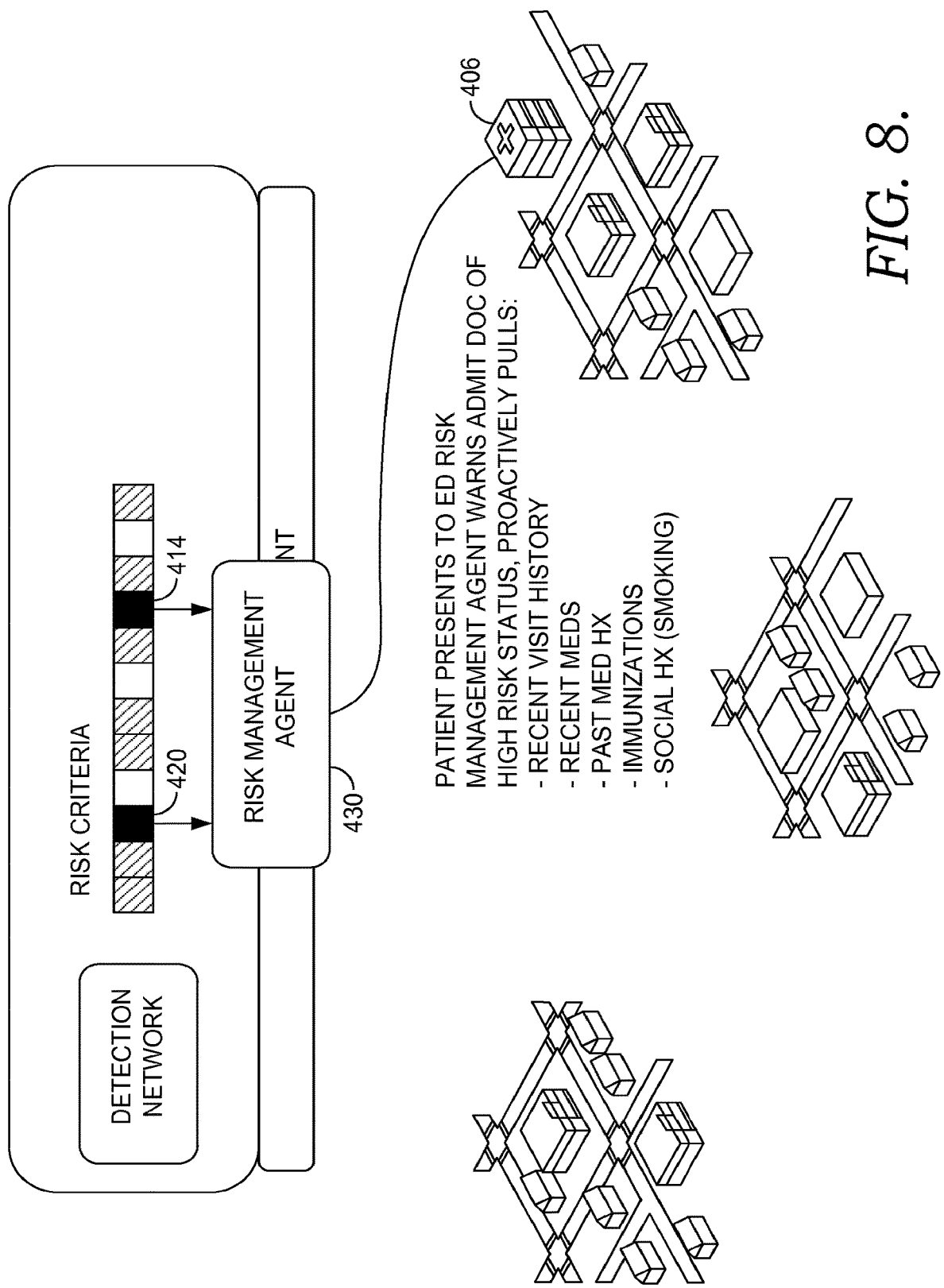

With reference to FIG. 8, when the patient later presents to the emergency department 406 at the local hospital, the risk management agent 430 of manager 408 warns the admitting emergency doctor of the patient's high-risk status for sepsis and proactively pulls and provides to the admitting emergency doctor the recent visit history for that same patient, a recent medication list, past medical history, immunization, and social history for the patient. Thus, the admitting emergency doctor is provided with an immediate picture of the patient's health over the last 48 hours based on the persistent state-based array that has been maintained by the manager 408 for the patient so that the treating clinician can quickly identify issues and quickly treat the patient if needed.

Figure 9A:
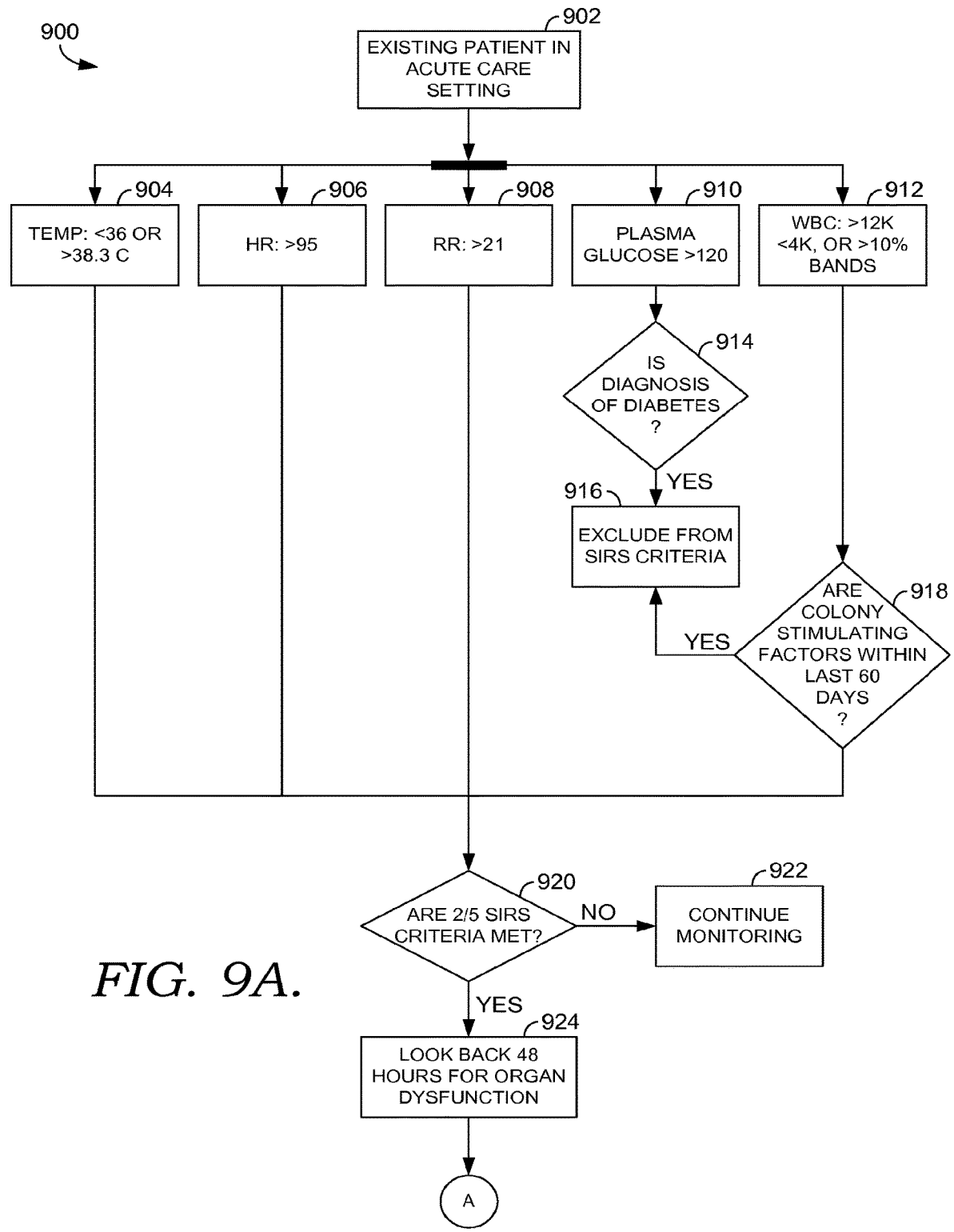
FIGS. 9A and 9B are flow diagrams of an exemplary algorithm of early detection logic using multi-site surveillance and decision support, in accordance with embodiments of the present invention.
Figure 9B:
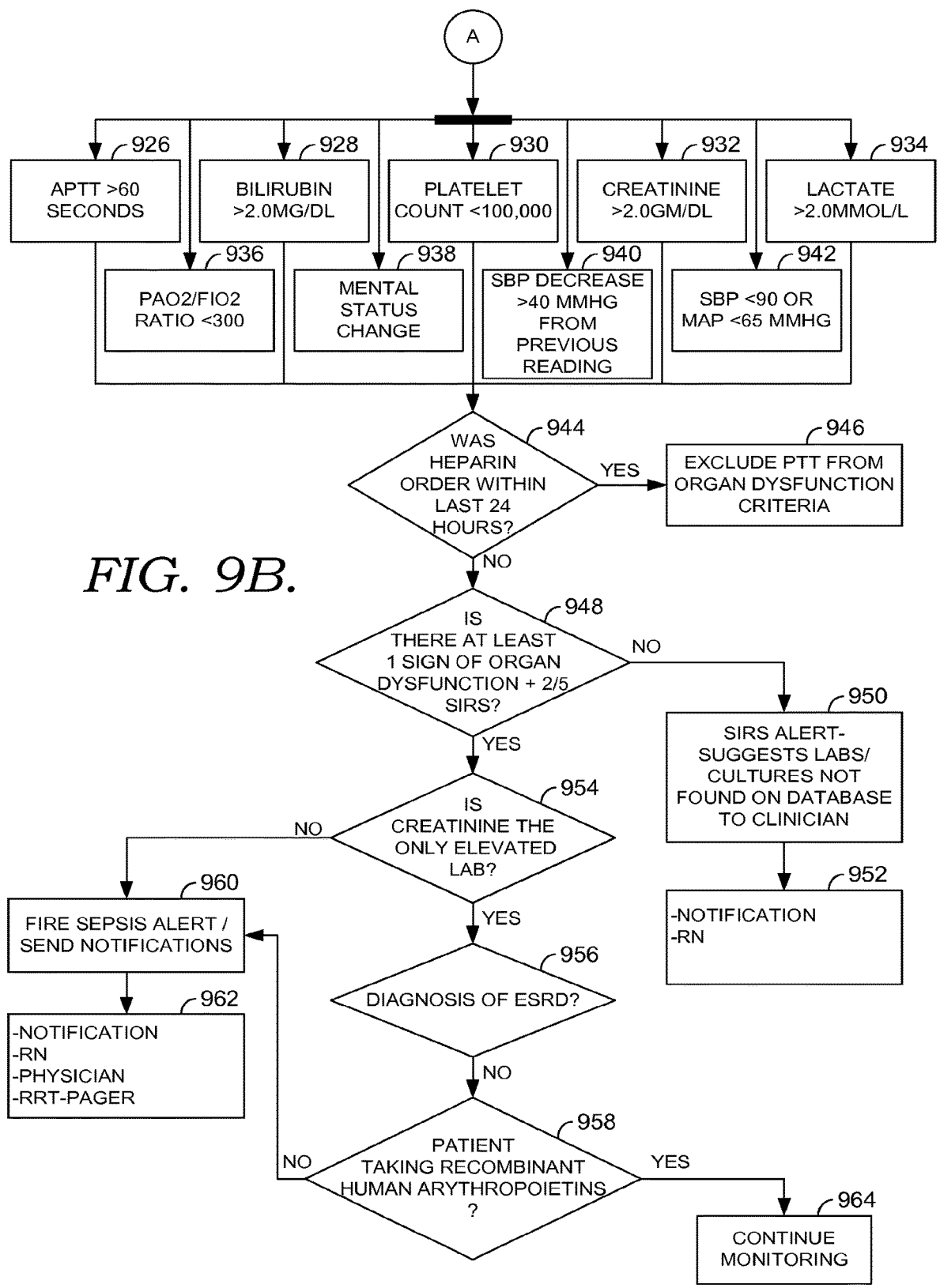

Turning now to FIGS. 9A and 9B, flow diagrams of an exemplary algorithm are illustrated of early detection logic using multi-site surveillance and decision support, in accordance with embodiments of the present invention. The algorithm illustrated in FIGS. 9A and 9B is specific for detecting that a patient is at risk for developing sepsis. Sepsis occurs in the presence of an infection with a systemic inflammatory response syndrome (SIRS) response. SIRS is a specific consequence to an infection, trauma, burn, or other offense. Sepsis affects nearly 750,000 Americans annually, resulting in a mortality rate of 28.6%. Each case of sepsis costs an additional $43,000 per case and extends the patient length of stay by an average of eleven days. Sepsis rates in the United States are expected to reach an incidence of one million cases a year by 2020. Annually, more Americans die from sepsis than either heart attack or stroke. Early detection is particularly important for sepsis because of the high-mortality rate and also because sepsis is difficult to diagnose, as fever, rapid pulse, and respiratory difficulties are found in many other disorders.

Initially, an existing patient is in an acute care setting, shown at box 902. The criteria typically used initially for detecting risk of sepsis include the patient's temperature, heart rate, respiratory rate, glucose level, blood glucose (capillary), and white blood cell count. Generally, the criteria include a variable or set of variables and an associated range or threshold(s) which is used for indicating the possible presence of sepsis (or another condition). For example, as shown in the exemplary algorithm, at box 904, the criteria for temperature is less than 36° C. or greater than 38.3° C. The criteria for heart rate at box 906 is greater than 95 bpm. The criteria for respiratory rate is greater than 21 breaths per minute, shown at box 908. The criteria for plasma glucose is greater than 120 mg/dL, shown at box 910. At box 912, the white blood cell count criteria is greater than 12,000 per mcL, less than 4,000 per mcL, or greater than 10% bands. For the plasma glucose at box 910, it is determined, at step 914, whether there has been a diagnosis of diabetes, as this affects the patient's blood/plasma sugar levels. If so, the glucose levels are excluded from the criteria for SIRS at step 916. For the white blood cell count at step 912, it is determined whether there have been colony stimulating factors within the previous 60 days at step 918. If so, the white blood cell count is excluded from the SIRS criteria. At step 920, it is determined whether at least two of the five SIRS criteria have been met. If not, the patient continues to be monitored at step 922. If at least two of the five SIRS criteria have been met, at step 924, organ dysfunction is analyzed from the previous 48 hours.

As described above in connection to FIGS. 21A and 21B, in some embodiments which use a multi-agent system 2130, different sets of criteria can be provided, wherein each set may include one or more variables each having an associated range or threshold. For example, one set of criteria provided might include (i) the temperature variable associated with a range, such as less than 36° C. or greater than 38.3° C.; (ii) the heart rate variable with threshold greater than 95 bpm.; (iii) respiratory rate variable with threshold greater than 21 breaths per minute; and (iv) white blood cell count with a range or thresholds of greater than 12,000 per mcL, less than 4,000 per mcL, or greater than 10% bands. Another set of criteria might have the same variables with different ranges or thresholds or might have more or less variables. For each set of criteria, an agent can be invoked to carry out the detection logic. Thus for example, one agent might handle the criteria described in connection to FIGS. 9A and 9B. For a different set of criteria provided, another agent is assigned to carry out the detection logic in parallel with the first agent (or in some embodiments the same agent might be used to serially carry out the detection logic on each set of criteria). Moreover, in addition to having different sets of criteria, as described above in connection to FIG. 21A, the detection logic used by each agent may vary. For example, at step 920, a first agent determines whether at least two of the five SIRS criteria have been met, and if so, proceeds to step 924. While another agent operating in parallel to the first agent determines if at least three of the total number of SIRS criteria have been met, and if so, proceeds to step 924.

Continuing to FIG. 9B, organ dysfunction utilizes several factors or variables, including, but not limited to lactic acid level, systolic blood pressure, mean arterial pressure, creatinine level, bilirubin total, platelet count, neurological symptoms, level of consciousness, whether hallucinations are present, behavior, Glasgow coma score, pediatric coma score, partial thromboplastin time (PTT), and $PaO_2/FiO_2$ ratio. Again as described above in connection to FIG. 9A, criteria include a variable or variables associated with a range or threshold(s). Accordingly, at box 926, the criteria shown for active PTT is greater than 60 seconds. The criteria for bilirubin at box 928 is greater than 2.0 mg/dL. The criteria for platelet count at box 930 is less than 100,000. The criteria for creatinine at box 932 is greater than 2.0 gm/dL. The criteria for lactate at box 934 is greater than 2.0 mmol/L. At box 936, the criteria for the ratio of $PaO_2/FiO_2$ is less than 300. At box 938, it is determined whether or not there has been a mental status change. At box 940, the criteria for systolic blood pressure (SBP) is a decrease of greater than 40 mmHg from the previous measurement or reading. Further, at box 942, an SBP of less than 90 or a mean arterial pressure (MAP) of less than 65 mmHg is the criteria for sepsis. At step 944, it is determined whether heparin was ordered within the last 24 hours. If so, PTT is excluded from the organ dysfunction criteria, shown at step 946.

If heparin was not ordered within the last 24 hours, it is determined, at step 948, whether there was at least one sign of organ dysfunction in addition to two or more out of the five SIRS criteria having been met. If not, a SIRS alert may be communicated at step 950 suggesting to the clinician various other labs and cultures not found on the database. If there is at least one sign of organ dysfunction in addition to at least two of the five SIRS criteria being met, it is determined whether creatinine is the only elevated lab at step 954. If so, it is determined whether the patient has been diagnosed with end stage renal disease (ESRD), shown at step 956. If the patient has not been diagnosed with ESRD, it is determined, at step 958, whether the patient is taking recombinant human erythropoietins. If so, the patient continues to be monitored at step 964. If either creatinine is the only elevated lab, determined at step 954, or the patient is not taking recombinant human erythropoietins, determined at step 958, a sepsis alert is communicated at step 960, which may include one or more of alerts and notifications to the various medical organizations, patient, primary care physician, etc. At step 962, notifications are communicated to one or more providers, including nurses, physicians, or other medical personnel and clinicians. As mentioned, alerts and notifications may be communicated through various mediums, including telephones, pagers, computers, PDAs, fax machines, or the like. Again, as described above in connection to FIGS. 9A, 21A and 21B, in some embodiments which use a multi-agent system 2130, different sets of criteria may be provided, wherein each set of criteria includes one or more variables each having an associated range or threshold. For each set of criteria, an agent is invoked to carry out the detection logic. Thus for example, one agent might handle the criteria described in connection to FIGS. 9A and 9B. For a different set of criteria provided, another agent is assigned to carry out the detection logic in parallel with the first agent (or in some embodiments the same agent might be used to serially carry out the detection logic on each set of criteria). Moreover, in addition to having different sets of criteria, as described above in connection to FIG. 21A, the detection logic, such as that of steps 944, 948, 954, 956, 958 used by each agent can vary. Thus, in some embodiments an agent may not perform one or more of these steps or may perform additional detection logic similar to these steps. For example, in some embodiments the logic applied by a first agent at step 948 determines if there is at least 1 sign of organ dysfunction in addition to at least two of the five SIRS criteria being met, and if so proceeds to step 954. While another agent operating in parallel to the first agent determines if there is at least 1 sign of organ dysfunction in addition to at least 3 of the total number of SIRS criteria being met, and if so, proceeds to step 954. Likewise yet another agent operating in parallel with the first two might determine if at least 2 signs of organ dysfunction are present in addition to at least 2 of the total SIRS criteria being met before proceeding to the logic of step 954.

FIGS. 10-12 illustrate tables 1000, 1100, and 1200 respectively, which each include exemplary actionable criteria and alerts for a patient being at risk for developing sepsis. In some embodiments using multi-agent system 2130, tables 1000, 1100, and 1200 are content tables 2124 of FIG. 21A. Further, in some embodiments, agents operating in parallel use criteria from tables 1000, 1100, and 1200 for determining a patient's risk for developing sepsis (or determining another condition). Accordingly, in some embodiments sets of criteria are provided by way of providing tables 1000, 1100, and 1200, so that each parallel-operating agent may access a table, or tables some cases, different than the table or tables accessed by the other parallel-operating agents. Alternatively, in some embodiments the same table is received by each parallel-operating agent, but each agent may not access in the same way all criteria included in the table, because for example, the detection logic employed by some agents is different than that of other agents. Accordingly, in some embodiments, health care providers or other clients desiring to test various ranges or thresholds of variables for a sepsis detection algorithm (or other condition-detection process), can suggest those ranges or thresholds by providing a new table such as table 1000, 1100, or 1200 (or updating an existing table), thereby resulting in causing an additional analysis to be performed by an agent using the criteria provided in the new (or updated) table.

Turning now to each of FIGS. 10, 11, and 12. FIG. 10 illustrates a table 1000 including exemplary actionable criteria and alerts for a patient being at risk for developing sepsis, in accordance with embodiments of the present invention. The table 1000 illustrates a results area 1010 indicting that two of five SIRS criteria are present, and that there is no organ dysfunction. The SIRS box 1012 illustrates the criteria for determining whether a patient is at risk for developing SIRS. For example, heart rate and temperature of the patient have been determined to put the patient at risk for SIRS, as the numerical values of these criteria have been met. Respiration, glucose, and the white blood cell count have been determined to be within normal limits. The organ dysfunction box 1014 illustrates that all tests are within the normal limits, including lactate, creatinine, platelet count, bilirubin, PTT, systolic blood pressure, mean arterial pressure, mental status change, and the $PiO_2/FiO_2$ ratio. Next, the alert box 1016 indicates that an alert has been communicated to the medical organizations whose clinicians have treated the patient, the primary care physician, and/or the like. Here, the alert states that the patient has met SIRS criteria that are listed in the alert. It also states that the physician should be contacted and it also suggests several laboratory tests that can be performed on the patient to further assess the patient's risk for developing SIRS and sepsis. These tests include lactate, creatinine, bilirubin, platelet count, PTT, blood cultures, and UA.

FIG. 11 illustrates a table 1100 including exemplary actionable criteria and alerts for a patient at risk for developing sepsis, in accordance with embodiments of the present invention. FIG. 11 is similar to FIG. 10 except that the criteria required to send an alert if three of the five SIRS criteria listed have been met based on the patient information, as shown in the results area 1110. Here, the heart rate, temperature, and respirations criteria have been met, as shown under the SIRS box 1112. The organ dysfunction box 1114 indicates that all tests for organ dysfunction are within normal limits. The alert box 1116 indicates that the alert is similar to the alert in FIG. 10, recommending that the physician be contacted and that several laboratory tests be ordered.

FIG. 12 illustrates a table 1200 including exemplary actionable criteria and alerts for a patient being at risk for developing sepsis, in accordance with embodiments of the present invention. FIG. 12 is also similar to FIGS. 10 and 11, but here, as indicated in the results box 1210, organ dysfunction criteria have been met. Like FIG. 10, two of the five SIRS criteria, shown under the SIRS box 1212, have been met, including heart rate and temperature. Under the organ dysfunction box 1214, the lactate measurement is outside of normal limits, and thus the system has indicated that there is a possibility of organ dysfunction. Under the alert box 1216, the alert states that the patient has met criteria for sepsis and organ dysfunction, and that the physician should be notified immediately so that the patient can be evaluated. It also states that early goal-directed therapy is essential for the treatment of sepsis, and that treatment is time dependent. In one embodiment, follow-up lab tests are also included in the alert.

FIG. 13 is an exemplary screen display of an alert after determination that a patient is at risk for developing sepsis, in accordance with an embodiment of the present invention. Along with the general alert information on the screen, an alert is shown. Alert area 1310 provides identifying information of the patient to whom the alert concerns. This area also indicates that the patient has met the criteria for being at risk for developing sepsis and states that the patient should be evaluated further. Alert area 1312 indicates that the patient has met a certain number of the SIRS criteria and outlines suggested laboratory tests that would be useful in further evaluating and treating the patient. Alert area 1314 provides the clinician with a useful outline of when the patient met each of the criteria, and if applicable, the numerical result for each criteria. Similarly, organ dysfunction criteria is shown, along with the date and results, if applicable. Some criteria may not have a numerical result, but instead may be a yes or no scenario. For instance, a box of the array may be "turned on" if the patient has a change in his or her mental condition. There may not be a numerical value that can be used in instances such as these. While FIG. 13 illustrates an exemplary alert, it should be noted that this is just one form of an alert that may be communicated when it is determined that a patient is at risk for developing a particular disease or condition, such as sepsis. For example, other embodiments may also provide a report of results of one or more parallel-operating agents, enabling a user or health care provider to receive feedback about the effectiveness of different criteria (such as suggested ranges of variables) and/or logic used for detecting the patient condition. In this manner, a user could be provided an opportunity to select one or more of the analyses, thereby providing some degree of feedback as to which analyses were accurate and which were not.

Figure 14:
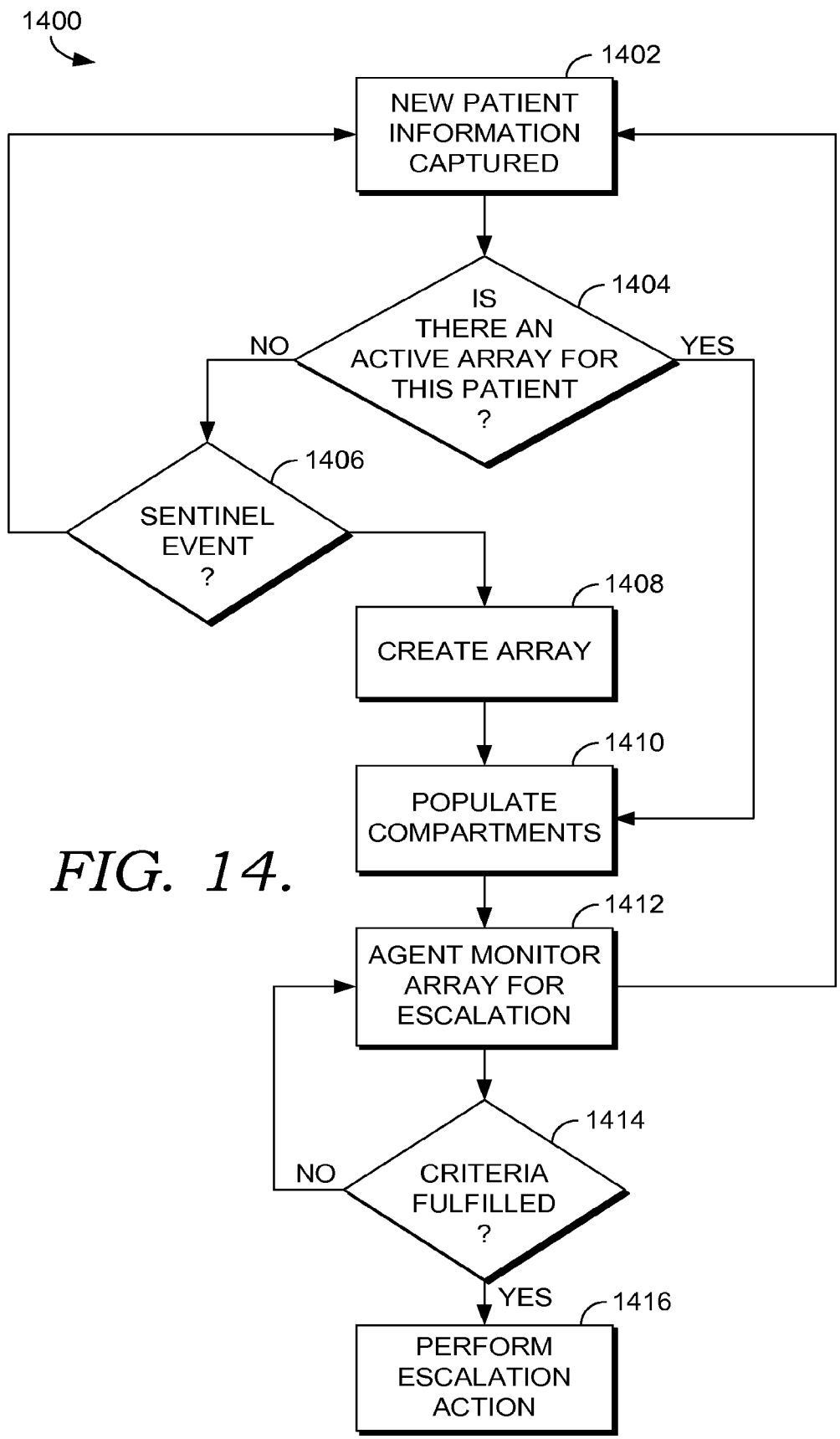
FIG. 14 is a flow diagram showing a method for monitoring patient information received from multiple sites in accordance with an embodiment of the present invention.

Referring next to FIG. 14, a flow diagram of a computer-implemented method 1400 for creating a multi-site persistent array of patient information and monitoring such information is provided. Initially, as shown at block 1402, patient information is received by the manager 202 of FIG. 2 from a medical organization or other source. At step 1404, it is determined whether there are one or more active arrays for the patient for whom patient information is received. For example, it may be determined whether a patient who is running a fever of 101.5 has an active array in the manager 202 for sepsis and/or infection risk. If an array does not exist for the patient for a particular condition, at step 1406, it is determined that an array should exist for a particular piece of information (sentinel event) received for the patient. For example, the system may determine that a patient running a fever of 101.5 degrees should have an array. At step 1408, the array for the patient for the identified potential condition or state is created.

At step 1410, the nodes or compartments of the array created are populated with relevant patient values and information. For example, if a fever is an identified node for sepsis, the value of the node for fever may be populated in the node or the node may be turned to positive for fever. The system continuously monitors for additional patient information coming for the patient with the open array and monitors the incoming patient information from different organizations for escalation over the defined period of time for the condition or state array. For example, a patient with a sepsis array may be continuously monitored for patient information related to risk factors for sepsis including, but not limited to, fever, rapid heart rate, rapid respiratory rate, elevated white blood cells, and elevated glucose.

At step 1414, it is determined whether a set number of nodes or patient criteria for the identified state or condition have been filled. If not, the system continues to monitor patient information for the array for escalation at step 1412. If it is determined that a set number of nodes or patient criteria received from multiple organizations have been fulfilled, the system performs escalation actions at step 1416 discussed above including alerting the provider and/or collecting patient information and records for presentation upon the next patient event.

Figure 15:
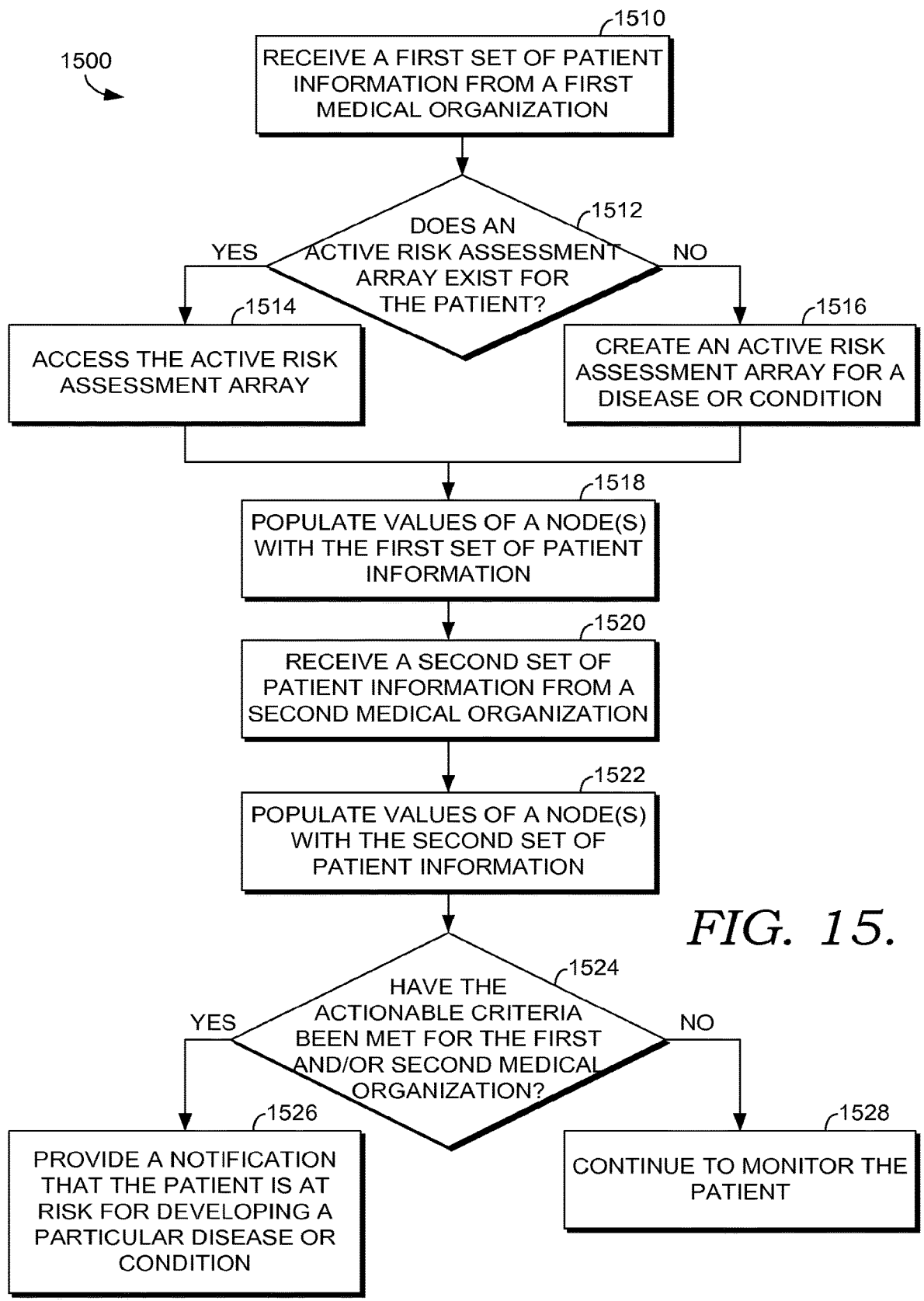
FIG. 15 is a flow diagram showing a method for enabling multi-site surveillance and decision support for a patient's medical care, in accordance with an embodiment of the present invention.

FIG. 15 is a flow diagram showing a method 1500 for enabling multi-site surveillance and decision support for a patient's medical care, in accordance with an embodiment of the present invention. Initially at step 1510, a first set of patient information is received from a first medical organization or other source. This set of patient information may include any number of types of information, including vitals, test results, mental conditions, physical conditions, etc. or other information as described in connection to patient information 2110 of FIG. 21A. At step 1512, it is determined whether an active risk assessment, which might be embodied as an assessment array, exists for the patient with which the patient information corresponds. As mentioned, an active risk assessment, assessment array, or simply an array, may exist for a particular disease or condition. Different arrays may have different nodes or categories that receive different types of patient information. For instance, for sepsis, a patient's temperature may be an important factor and one of the criteria used to determine whether a patient is at risk for sepsis, but for substance abuse, a patient's temperature may be irrelevant. Further, arrays may exist for a predetermined amount of time, which may vary from hours to years, depending on the disease or condition represented by the array. For instance, an array for sepsis may exist for 24-48 hours, while an array for substance abuse or a mental condition may persist in the system for several years. As such, step 1512 of determining whether an active array exists may go even further to determine whether the patient information received is even related to the array, if an array currently exists for the patient.

If it is determined that an active array currently exists, the array is accessed by the system at step 1514. If not, an active risk assessment array may be created at step 1516 for a particular disease or condition. At this point, it may not be known what the patient is at risk for developing, and as such more than one array may be created so that the patient can be monitored for multiple diseases or conditions for which he or she may be at risk for developing. If the patient, based upon a previous condition or a previous operation, may be at risk for developing SIRS or sepsis, an array corresponding to these conditions may be created. At step 1518, values of one or more nodes are populated with the first set of patient information or at least a portion thereof, as some of the information may not be relevant or necessary for use with an array. Values of a node may include numerical values (e.g., a patient's temperature, heart rate, lab test results), alpha-numerical values, or simply may be turned "on" or "off" if the node represents whether the patient has a mental condition or does not, for example. Or, even if the node represents a patient's temperature, the node may be turned "on" or "off" depending on whether the patient's temperature meets the criteria or not.

At step 1520, a second set of patient information is received from a second medical organization or other source. In one embodiment, the first and second medical organizations have distinct medical record systems, such as different companies that store and monitor their medical records. The second set of patient information may represent the patient's visit to a health care facility for something related to the visit that produced the first set of patient information, or for something completely unrelated. Even if unrelated, the patient information may turn out to be related as being used in a single array to make the determination that the patient is at risk for a particular disease or condition. In some embodiments, patient identity management services, such as that described in connection to identity management 214 of FIG. 2, are employed to determine whether for a particular patient, patient information exists from other sources, such as other medical organizations using a distinct medical record system. Thus, patient information from multiple sources (such as different medical organizations) is associated with the same patient and thus available for populating an active risk assessment for that patient.

At step 1522, the values of one or more nodes are populated with the second set of patient information, or at least a portion thereof. It is determined at step 1524 whether actionable criteria have been met for the first and/or second medical organization. In one embodiment, the monitoring system determines the criteria that are to be used, but in an alternative embodiment, each medical organization is able to establish its own criteria. As such, the first medical organization may receive an alert before the second medical organization if the criteria of the first medical organization are generally more stringent and conservative. In this scenario, the second medical organization may at least receive a notification indicating that the first medical organization received an alert based on its criteria. In some instances, this may prompt the second medical organization to reevaluate and determine whether it needs to further evaluate the patient for the particular disease or condition. When the criteria of the second medical organization are met, the second medical organization would then receive an alert.

If the actionable criteria have been met at step 1526, a notification is provided that the patient is at risk for developing a particular disease or condition. The notification may comprise an alert, and may take on one of many forms, as previously mentioned. If the actionable criteria have not been met, the patient continues to be monitored at step 1528 by way of the active risk assessment array. In one embodiment, the criteria are sepsis-specific actionable criteria, as they apply specifically to sepsis. The nodes of this array specific to sepsis may include, for example, a heart rate, body temperature, respiration rate, white blood cell count, glucose, bands, lactate level, systemic blood pressure, mean arterial pressure, oxygen saturation, creatinine, bilirubin, platelet count, partial thromboplastin time (PTT), and $PaO_2/FiO_2$ ratio.

While FIG. 15 illustrates two medical organizations that send patient information, the patient information my come from any number of medical organizations or sources. For instance, in one embodiment, a third set of patient information is received from a third medical organization that maintains a different medical record system than the first and second medical organizations. In some embodiments, the third set of patient information is associated with the first and second sets based on knowledge that they correspond to the common patient. In some embodiments, patient identity management services, such as described in connection to identity management 214 of FIG. 2, are employed to determine matching sets of patient information, which may come from different sources, for a particular patient. Continuing this example having a third set of patient information from a third medical organization, values of a third set of nodes of the active risk assessment array are populated with the third set of patient information.

Figure 22:
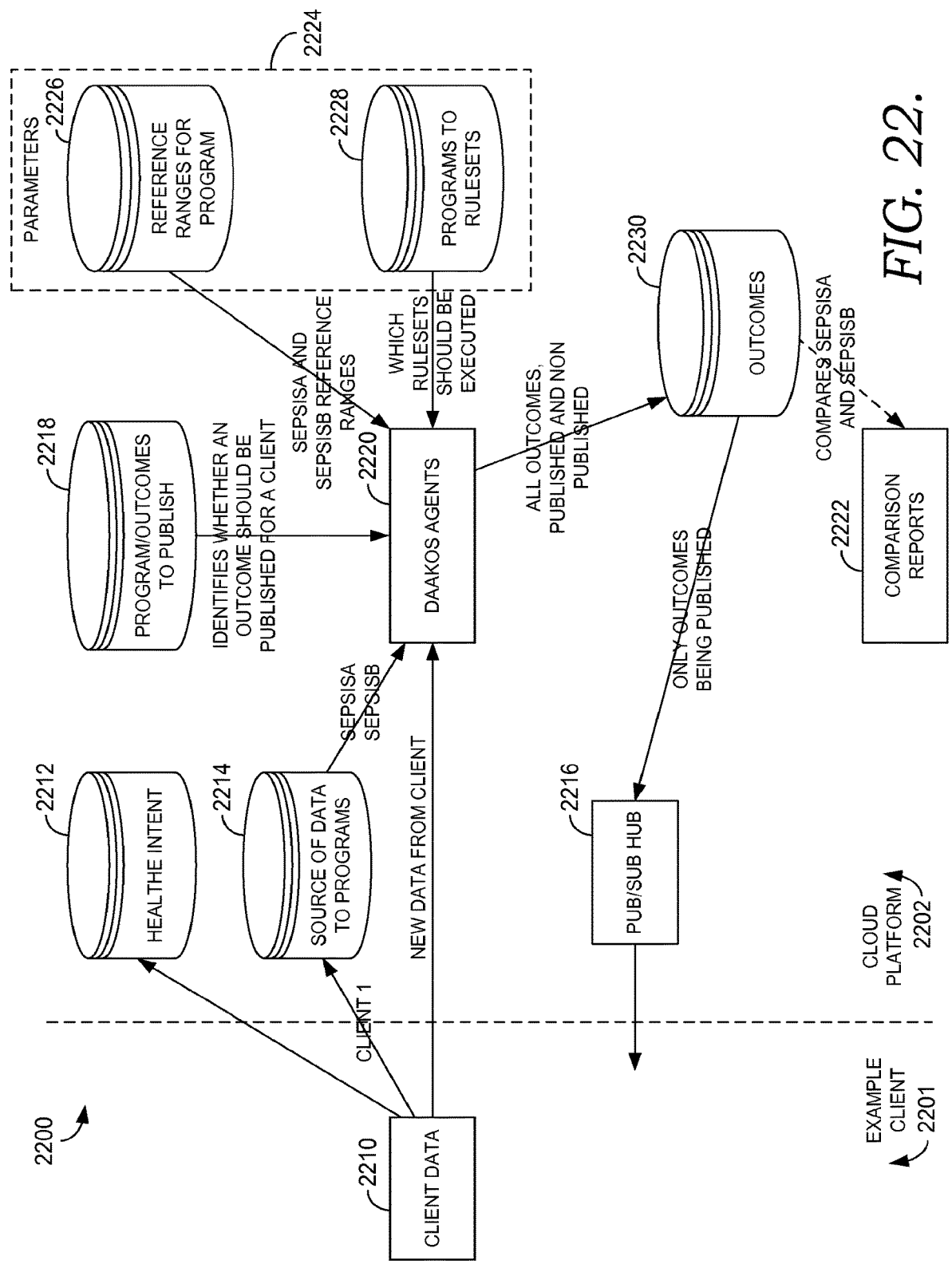
FIG. 22 depicts a block diagram of an exemplary system for enabling simulation of two algorithms for determining a patient's risk of sepsis to provide decision support for a patient's medical care, in accordance with an embodiment of the present invention.

Turning now to FIG. 22, with continuing reference to FIGS. 21A and 21B, a block diagram of an exemplary system 2200 is shown for enabling simulation of multiple algorithms for determining a patient's risk for sepsis to provide decision support for a patient's medical care, in accordance with an embodiment of the present invention. Example system 2200 further shows an example embodiment for simulating two algorithms for determining a patient's risk for sepsis performed with two sets of criteria and logic, the algorithms referred to herein as Sepsis A and Sepsis B. As shown in this example embodiment, Client's data 2210 from example client 2201, includes information about a patient and might be provided from one or more medical organizations or other sources, and is made accessible to cloud platform 2202. In some embodiments cloud platform 2202 includes cloud-computing platform 212 and support manager 202 of FIG. 2, which can be embodied as system 2100 of FIG. 21A, in some embodiments. Client's data 2210 is provided to Healthe Intent 2212, data store 2214, and to DAAKOS agents 2220. Healthe Intent 2212 facilitates health care services including managing patient care and accessing patient information. Data store 2214 provides sources of data to agents running parallel simulations (here Sepsis A and Sepsis B) of sepsis detection. DAAKOS agents 2220 include one or more agents 2135 of FIG. 21A, and further receive information from data store 2218 regarding which simulation output to publish. For example, agents accessing data store 2218 may determine whether the outcome from Sepsis A or Sepsis B should be published. In embodiments, information about which output to publish is updatable by an agent or health care provider. Thus, for example, if it is determined that a particular algorithm, such as Sepsis C, is the superior algorithm based on its performance and/or characteristics of the available patient information, then data store 2218 can be updated to indicate that Sepsis C is to be published, and other outcomes (e.g., Sepsis A and Sepsis B) are to be merely compared for efficiency against Sepsis C, in some embodiments. In some embodiments, an association, which may be embodied as a table, manifest, or database entry, for example, is maintained in data store 2218 which identifies which algorithm's outcome is to be published, and in some embodiments associates various patient information with various algorithms, so that for a given set of patient information available, one algorithm's outcome can be chosen to be the published outcome.

Agents 2220 also receive parameters 2224, which include parameters 2120 of FIG. 21A, in some embodiments. As shown in the example embodiment of FIG. 22, parameters provided to agents 2220 include reference ranges 2226 and programs to rule sets 2228. In some embodiments, reference ranges 2226 are examples of criteria, described above in connection to FIGS. 9A and 9B, and programs to rule sets 2228 are examples of detection logic, also described above in connection to FIGS. 9A and 9B.

Although parameters 2224 is shown in this example to include only reference ranges 2226 and programs to rule sets 2228, it could be considered to include data store 2218, which provides parameters, such as parameters 2120 of FIG. 21A, to agents in the form of an indication of which outcomes are to be published. Moreover, as discussed above, although six separate data stores are shown in the example of FIG. 22, these data stores may be embodied on the same data store, distributed across a number of data stores, or stored in the cloud.

Agents 2220 perform analyses on algorithms Sepsis A and Sepsis B and store outcomes in data store 2230. At block 2222 the outcomes of Sepsis A and Sepsis B are compared. In some embodiments, the results of the comparison may be provided (not shown) to a health care provider or other user or used to determine which outcome should be published for future analyses. Thus in some embodiments the comparison of reports 2222 is accessible to a user through, for example, user interface 2140 of FIG. 21A. At block 2216 the outcome or outcomes designated for publishing are received and published to example client 2201.

In the example of FIG. 22, the results of the two algorithms Sepsis A and Sepsis B, included the following results, shown in Table 1 below, from a reduction to practice performed in Feb. 12, 2012.

| Sepsis A | Sepsis B |
| --- | --- |
| Total SIRS Outcomes: 54 | Total SIRS Outcomes: 25 |
| 3 Criteria for sepsis 46 | 3 Criteria for sepsis 16 |
| 4 Criteria for sepsis 8 | 4 Criteria for sepsis 9 |
| Total Sepsis Antibiotics Outcomes: 1430 | Total Sepsis Antibiotics Outcomes: 331 |
| Sepsis Alert Anti-infection 1430 | Sepsis Alert Anti-infection 331 |
| Total Sepsis Outcomes: 486 | Total Sepsis Outcomes: 274 |
| Alert for Sepsis 486 | Alert for Sepsis 274 |

As can be understood, embodiments of the invention provide action-based deep links for search results. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages, which are obvious and inherent to the system and method. It will be understood that certain features and subcombinations are of utility and may be employed without reference to other features and subcombinations. This is contemplated by and is within the scope of the claims.

What is claimed is:

1. A method for detecting a clinical condition of a human patient using a multi-agent computer system, the method comprising:
   generating a risk assessment array for the human patient representing the patient's risk of developing the clinical condition, the risk assessment array comprising a computing data structure including a plurality of state nodes, each state node corresponding to a distinct condition parameter associated with a set of patient information and each state node being updateable by the multi-agent computer system;
   utilizing a first computing agent stored on the multi-agent computer system, having a first set of agent parameters, and a second computing agent stored on the multi-agent computer system, having a second set of agent parameters to monitor the risk assessment array for at least one time sensitive actionable criteria, in parallel;
   determining, by the multi-agent computer system, that the second computing agent detected that the at least one time sensitive actionable criteria has been met based on the monitoring of the risk assessment array, at a time that the first computing agent has not detected that the at least one time sensitive actionable criteria has been met;
   automatically invoking a dynamic swap of the second computing agent with the first computing agent using the multi-agent computer system; and
   subsequent to invoking the dynamic swap, associating the second computing agent with the human patient, and causing the first computing agent to cease monitoring the risk assessment array.

2. The method of claim 1, wherein the multi-agent computer system automatically invokes the dynamic swap without recompiling or reconfiguring the multi-agent computer system.

3. The method of claim 1, further comprising:
   determining, by the multi-agent computer system, that a third computing agent detected that the at least one time sensitive actionable criteria has been met, before the first computing agent; and
   automatically invoking a dynamic swap of the first computing agent with the third computing agent.

4. The method of claim 1, further comprising:
   receiving specific patient information;
   based on the specific patient information, updating, by the multi-agent computer system, the time sensitive actionable criteria.

5. The method of claim 4, further comprising:
   based at least in part on updating the logic, determining that a third computing agent detected that the at least one time sensitive actionable criteria has been met, before the first computing agent; and automatically invoking a dynamic swap of the first computing agent with the third computing agent.

6. The method of claim 1, wherein the time sensitive actionable criteria is associated with a risk of developing sepsis.

7. The method of claim 1, further comprising providing feedback information to a user of the multi-agent computer system to enable streamlining care of future patients, wherein the feedback information comprises at least one variable.

8. One or more non-transitory computer storage media having computer-executable instructions embodied thereon, that when executed by a computing system having a processor and memory, cause the computing system to perform a method for detecting a clinical condition of a human patient, the method comprising:
generating a risk assessment array for the human patient representing the patient's risk of developing the clinical condition, the risk assessment array comprising a computing data structure including a plurality of state nodes, each state node corresponding to a distinct condition parameter associated with a set of patient information and each state node being updateable by the multi-agent computer system;
utilizing a first computing agent stored on the multi-agent computer system, having a first set of agent parameters, and a second computing agent stored on the multi-agent computer system, having a second set of agent parameters to monitor the risk assessment array for at least one time sensitive actionable criteria, in parallel;
determining, by the multi-agent computer system, that the second computing agent detected that the at least one time sensitive actionable criteria has been met based on the monitoring of the risk assessment array, at a time that the first computing agent has not detected that the at least one time sensitive actionable criteria has been met;
automatically initiating a dynamic swap of the second computing agent with the first computing agent using the multi-agent computer system;
subsequent to invoking the dynamic swap, associating the second computing agent with the human patient, and causing the first computing agent to cease monitoring the risk assessment array.

9. The media of claim 8, wherein the time sensitive actionable criteria is associated with a risk of congestive heart failure.

10. The media of claim 8, further comprising providing an alert to the human patient, to a provider of the human patient, or to a medical organization, the alert corresponding to the time sensitive actionable criteria.

11. The media of claim 8, wherein the monitoring by the first computing agent comprises:
communicating with other computing agents; and
receiving transformed data from at least one other computing agent, wherein the transformed data is transformed from incomplete data, outdated data, or uncertain data.

12. The media of claim 8, wherein the multi-agent computer system further comprises domain specific agents for managing local domain-specific resources.

13. The media of claim 8, wherein the multi-agent computer system automatically initiates the dynamic swap without recompiling or reconfiguring the multi-agent computer system.

14. The media of claim 8, further comprising:
utilizing a third computing agent stored on the multi-agent computing system, having a third set of agent parameters to monitor the risk assessment array.

15. The media of claim 8, further comprising:
wherein prior to the dynamic swap of the second computing agent with the first computing agent, the second computing agent is utilized for detecting the clinical condition, and after the dynamic swap of the second computing agent with the first computing agent, the first computing agent is utilized for detecting the clinical condition.

16. The media of claim 8, wherein the monitoring comprise evaluating medical records of different medical organizations that are relevant for the human patient and the clinical condition.

17. A multi-agent computer system for detecting a clinical condition of a human patient, the multi-agent computer system comprising:
at least two computing agents;
at least one processor; and
one or more non-transitory computer storage media having computer-executable instructions embodied thereon, that when executed by the at least one processor or the multi-agent computer system, cause the multi-agent computer system to perform a method for detecting the clinical condition of the human patient, the method comprising:
generating a risk assessment array for the human patient representing the patient's risk of developing the clinical condition, the risk assessment array comprising a computing data structure including a plurality of state nodes, each state node corresponding to a distinct condition parameter associated with a set of patient information and each state node being updateable by the multi-agent computer system;
utilizing a first computing agent stored on the multi-agent computer system, having a first set of agent parameters, and a second computing agent stored on the multi-agent computer system, having a second set of agent parameters to monitor the risk assessment array for at least one time sensitive actionable criteria, in parallel;
determining, by the multi-agent computer system, that the second computing agent detected that the at least one time sensitive actionable criteria has been met based on the monitoring of the risk assessment array, at a time that the first computing agent has not detected that the at least one time sensitive actionable criteria has been met;
automatically initiating a dynamic swap of the second computing agent with the first computing agent using the multi-agent computer system; and
subsequent to invoking the dynamic swap, associating the second computing agent with the human patient, and causing the first computing agent to cease monitoring the risk assessment array.

18. The system of claim 17, the method further comprising:
receiving from at least a first medical organization and a second medical organization, patient information comprising clinical data corresponding to the human patient;
reconciling terms, of the patient information, used by the first medical organization and the second medical organization; and
evaluating, using the first computing agent and the second computing agent, the patient information comprising the reconciled terms.

19. The system of claim 17, the method further comprising evaluating the clinical condition by the first computing agent and the second computing agent, wherein the evaluating comprises detecting the clinical condition using detection logic corresponding to the clinical condition, and wherein the first computing agent and the second computing agent perform the evaluating in parallel.

20. The system of claim 17, wherein the multi-agent computer system automatically initiates the dynamic swap without recompiling or reconfiguring the multi-agent computer system.

* * * * *